(12) United States Patent
Ryan et al.

(10) Patent No.: US 10,052,220 B2
(45) Date of Patent: Aug. 21, 2018

(54) STOMACH BYPASS FOR THE TREATMENT OF OBESITY

(75) Inventors: Shawn Ryan, Upton, MA (US); Barry Weitzner, Acton, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 1090 days.

(21) Appl. No.: 12/900,984

(22) Filed: Oct. 8, 2010

(65) Prior Publication Data
US 2011/0087146 A1    Apr. 14, 2011

Related U.S. Application Data

(60) Provisional application No. 61/250,305, filed on Oct. 9, 2009.

(51) Int. Cl.
| | |
|---|---|
| *A61F 2/04* | (2013.01) |
| *A61F 5/00* | (2006.01) |
| *A61F 2/07* | (2013.01) |

(52) U.S. Cl.
CPC .............. *A61F 5/0076* (2013.01); *A61F 2/04* (2013.01); *A61F 2/07* (2013.01); *A61F 2002/044* (2013.01); *A61F 2002/045* (2013.01)

(58) Field of Classification Search
USPC ............................................................ 604/8
See application file for complete search history.

(56) References Cited

U.S. PATENT DOCUMENTS

| | | | | |
|---|---|---|---|---|
| 4,501,264 A | * | 2/1985 | Rockey | A61F 5/00 128/898 |
| 4,763,653 A | * | 8/1988 | Rockey | A61B 17/12 604/103.07 |
| 6,146,389 A | * | 11/2000 | Geitz | A61F 2/95 600/121 |
| 6,302,917 B1 | * | 10/2001 | Dua | A61F 2/04 623/23.64 |
| 6,540,789 B1 | * | 4/2003 | Silverman | A61B 17/00234 600/29 |
| 7,037,344 B2 | * | 5/2006 | Kagan | A61F 2/04 606/151 |
| 7,220,237 B2 | * | 5/2007 | Gannoe | A61B 17/072 128/898 |
| 2002/0183768 A1 | * | 12/2002 | Deem | A61B 17/064 606/151 |
| 2003/0040804 A1 | * | 2/2003 | Stack | A61F 2/04 623/23.7 |

(Continued)

FOREIGN PATENT DOCUMENTS

WO    2007/121028 A2    10/2007

OTHER PUBLICATIONS

International Search Report for International Application No. PCT/US2010/052021 dated Mar. 17, 2011.

(Continued)

*Primary Examiner* — Tatyana Zalukaeva
*Assistant Examiner* — Guy K Townsend
(74) *Attorney, Agent, or Firm* — Fay Kaplun & Marcin, LLP

(57) ABSTRACT

The present application provides devices and methods for inducing weight loss. In particular, the present application provides devices which are secured in the stomach or external to the stomach to reduce digestion and/or absorption of food in accordance with the methods of the invention.

18 Claims, 27 Drawing Sheets

(56) References Cited

U.S. PATENT DOCUMENTS

| | | | |
|---|---|---|---|
| 2003/0158601 A1* | 8/2003 | Silverman | A61B 17/00234 623/14.13 |
| 2003/0199991 A1* | 10/2003 | Stack | A61F 2/04 623/23.65 |
| 2003/0220660 A1* | 11/2003 | Kortenbach | A61B 17/0643 606/151 |
| 2004/0039452 A1* | 2/2004 | Bessler | A61F 2/07 623/23.65 |
| 2004/0089313 A1* | 5/2004 | Utley | A61B 18/1492 128/898 |
| 2004/0092892 A1* | 5/2004 | Kagan | A61F 2/04 604/264 |
| 2004/0107004 A1* | 6/2004 | Levine | A61B 17/0401 623/23.64 |
| 2004/0117031 A1 | 6/2004 | Stack et al. | |
| 2004/0138760 A1 | 7/2004 | Schurr | |
| 2004/0172142 A1* | 9/2004 | Stack | A61F 2/04 623/23.65 |
| 2004/0220682 A1* | 11/2004 | Levine | A61F 5/0076 623/23.65 |
| 2005/0049718 A1* | 3/2005 | Dann | A61F 2/04 623/23.65 |
| 2005/0125075 A1* | 6/2005 | Meade | A61B 17/0401 623/23.64 |
| 2005/0177181 A1* | 8/2005 | Kagan | A61B 17/00234 606/151 |
| 2005/0228504 A1 | 10/2005 | Demarais | |
| 2005/0273060 A1* | 12/2005 | Levy | A61B 17/1114 604/192 |
| 2006/0020247 A1* | 1/2006 | Kagan | A61B 17/00234 604/264 |
| 2007/0265709 A1* | 11/2007 | Rajan | A61F 2/04 623/23.64 |
| 2007/0282452 A1* | 12/2007 | Weitzner | A61F 2/04 623/23.7 |
| 2007/0282453 A1* | 12/2007 | Weitzner | A61F 2/04 623/23.7 |
| 2008/0228126 A1* | 9/2008 | Bessler | A61F 2/04 604/9 |
| 2008/0249635 A1* | 10/2008 | Weitzner | A61F 5/0003 623/23.65 |

OTHER PUBLICATIONS

Written Opinion of the International Searching Authority for International Application No. PCT/US2010/052021 dated Mar. 17, 2011.

\* cited by examiner

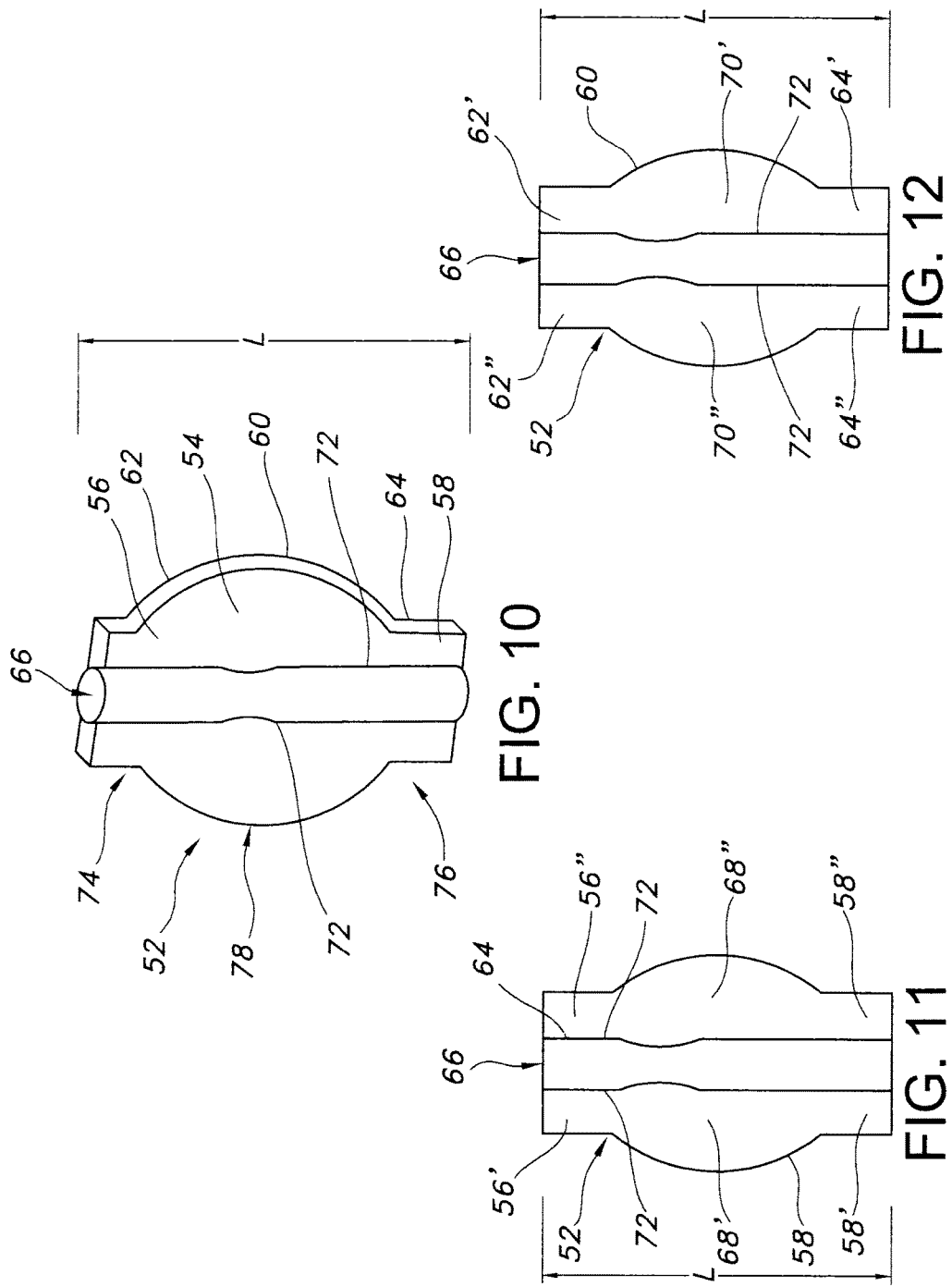

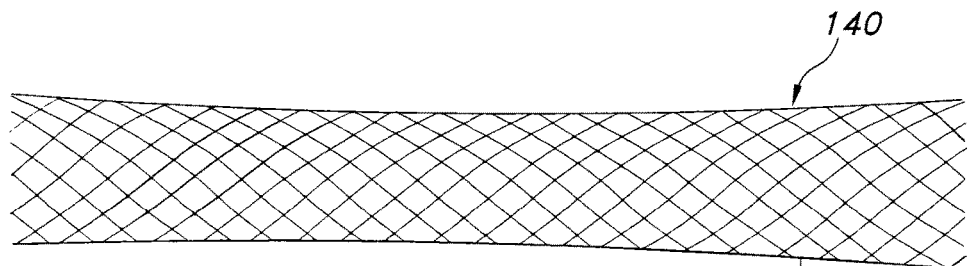
FIG. 25
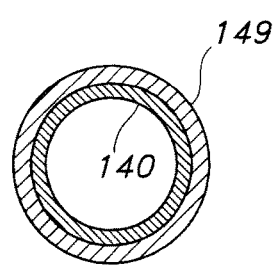 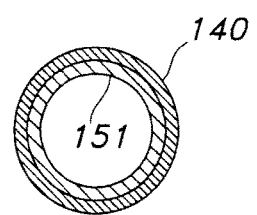 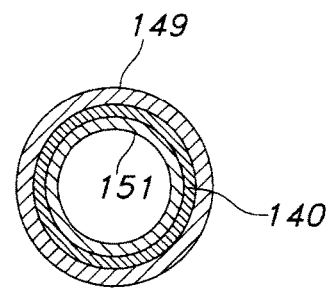
FIG. 26  FIG. 27  FIG. 28
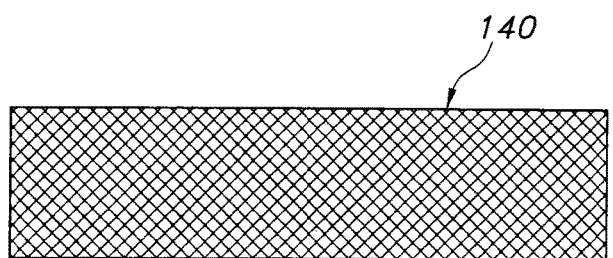
FIG. 29
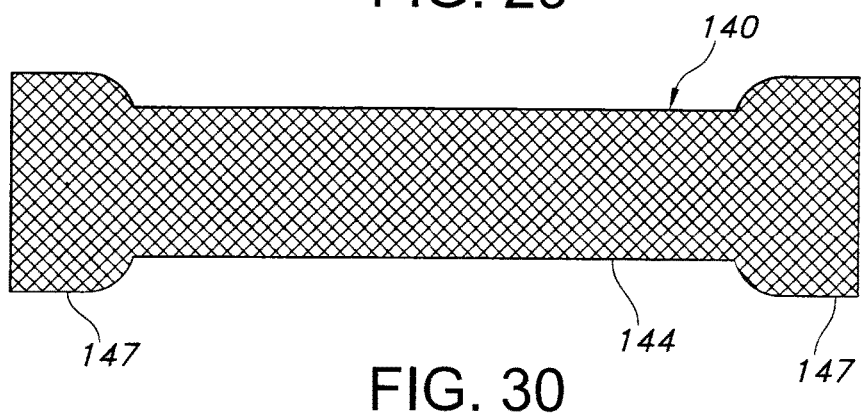
FIG. 30

STOMACH BYPASS FOR THE TREATMENT OF OBESITY

CROSS-REFERENCE TO RELATED APPLICATION

This application claims the benefit of U.S. Provisional Application No. 61/250,305, filed Oct. 9, 2009, the entire contents of which are incorporated herein by reference.

FIELD OF THE INVENTION

The present invention relates generally to anti-obesity devices and methods for using the same. More specifically, the present invention relates to anti-obesity devices which are secured in the stomach or external to the stomach to reduce digestion and/or absorption of food.

BACKGROUND OF THE INVENTION

Obesity is a major health issue in the United States and in many nations throughout the world. Obesity leads to increased risk of premature death and increased risk of comorbid conditions such as type II diabetes, hypertension, and heart disease. Approximately, one-third of U.S. adults are obese, i.e., have a body-mass index (BMS) greater than 30.

Current treatments for obesity include diet, exercise, drugs, and surgery. Non-surgical treatments have shown little effectiveness, and surgery is typically indicated only for those individuals who are morbidly obese, i.e., for those who have a BMS of greater than 40 or for those individuals who have a BMS of greater than 35 with a comorbid condition. Surgical interventions include restrictive interventions which limit food intake, malabsorptive interventions which limit nutrient absorption, and combinations thereof, i.e., interventions which both limit food intake and limit nutrient absorption. One of the most effective surgical procedures is the Roux-en-Y gastric bypass, which is a combination surgery to create a small stomach pouch (to limit food intake) and to bypass sections of the intestine responsible for absorption. Roux-en-Y gastric bypass, however, is normally irreversible.

In the normal workings of the gastrointestinal system, food travels from the mouth and then through the esophagus to the stomach. In the stomach, gastric juice is secreted and mixes with the food to produce chyme, i.e., partially digested food. The chyme then empties into the small intestine through the pylorus, i.e., the region of the stomach which connects to the duodenum. In the small intestine, chyme mixes with digestive fluids. In particular, in the duodenum (i.e., the upper portion of the small intestine which is proximate to the stomach), chyme mixes with bile and pancreatic fluid.

As a result of the mixing of chyme with digestive fluids including pancreatic fluid and bile in the small intestine and, more particularly, in the duodenum, chyme is chemically broken down so that nutrients contained therein may be absorbed across the wall of the small intestine. Specifically, carbohydrates are broken down into simple sugars, proteins are broken down into amino acids, and fats are broken down into fatty acids. Pancreatic fluid and, more particularly, the digestive enzymes contained therein, aid(s) in the digestion of proteins, carbohydrates, and fats, while bile aids in the emulsification, digestion, and absorption of fats. Reabsorption of the products of digestion and, more particularly, reabsorption of fatty acids and simple sugars in the duodenum, however, can ultimately lead to the deposition of fat deposits in the body and, consequently, weight gain.

In view of the foregoing, methods which modify the normal workings of the gastrointestinal system to minimize digestion of food in the stomach and to minimize the digestion of fats and carbohydrates and the reabsorption of the products of digestion (particularly, fatty acids and simple sugars) in the duodenum would be useful for treating individuals who are overweight and, more particularly, individuals who are obese.

The need exists for low cost, less invasive interventions for the treatment of obesity, including morbid obesity.

BRIEF DESCRIPTION OF THE DRAWINGS

FIG. 10 is a perspective view of an uninflated anti-obesity device in accordance with the present invention.

FIG. 11 is a front view of the anti-obesity device shown in FIG. 10.

FIG. 12 is a back view of the anti-obesity device shown in FIGS. 10 and 11.

FIG. 25 is an exploded view of a stent for use in the subject invention.

FIG. 26 is a cross-sectional view of the stent of FIG. 25 illustrating an outer graft covering disposed on the stent.

FIG. 27 is a cross-sectional view of the stent of FIG. 25 illustrating an inner graft lining disposed on the stent.

FIG. 28 is a cross-sectional view of the stent of FIG. 25 illustrating an inner graft lining and an outer graft covering disposed on the stent.

FIG. 29 is a side planar view of a stent for use in the subject invention illustrating a substantially longitudinally straight stent.

FIG. 30 is a side planar view of a stent illustrating outwardly flared ends according to the present invention.

Corresponding reference characters indicate corresponding parts throughout the several views of the drawings.

SUMMARY OF THE INVENTION

Figure 1:
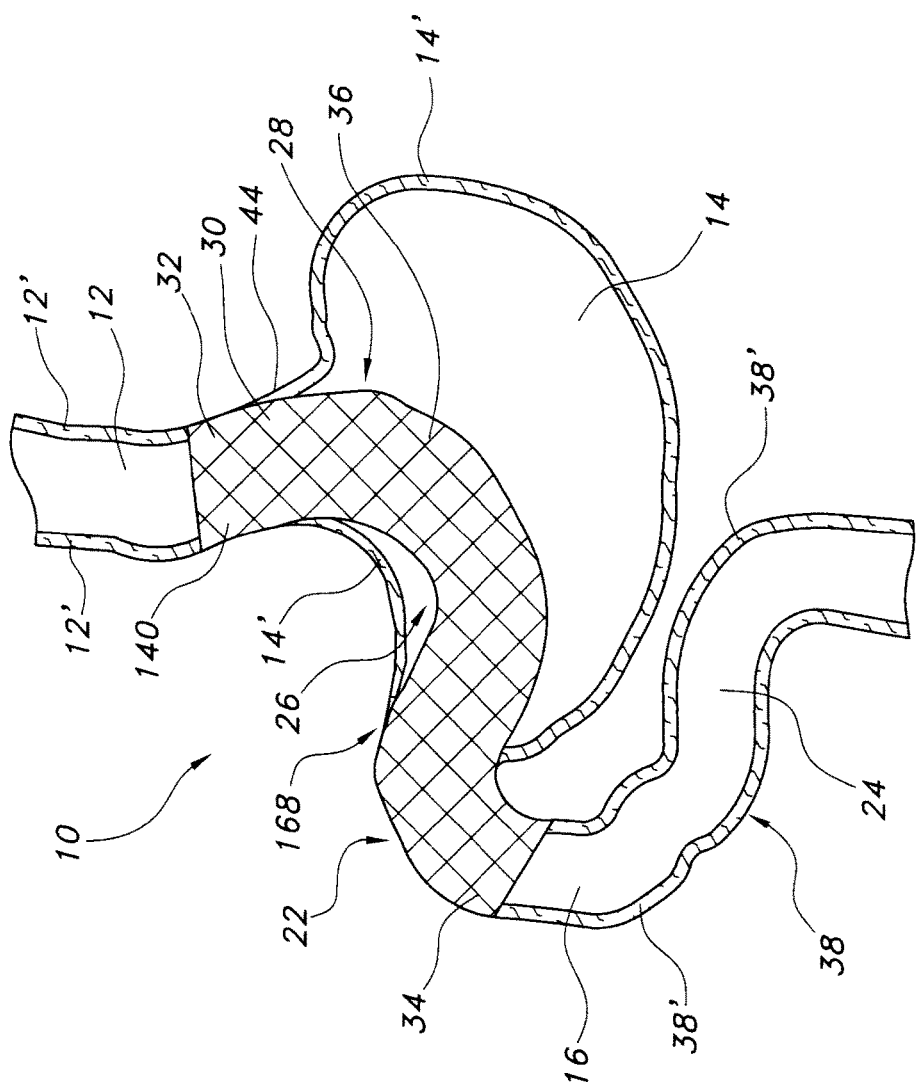
FIG. 1 is an anatomical elevational view of a stomach and adjacent esophagus and small intestine, the wall of the stomach, esophagus, and small intestine being broken away to show an anti-obesity device in accordance with the present invention.

The present invention provides devices and methods for inducing weight loss in an individual. In some embodiments, the present invention provides devices which may be placed in a stomach in accordance with the methods of the present invention to reduce or eliminate digestion in the stomach, thereby inducing weight loss. In other embodiments, the present invention provides devices which may be placed external to the stomach in accordance with methods of the present invention to eliminate digestion in the stomach, thereby inducing weight loss. In particular, in some embodiments, the present invention provides a device and method for bypassing both the stomach and for bypassing the duodenum either partially or completely. As a result, the amount of digestion and the amount absorption of the products of digestion are reduced, consequently inducing weight loss.

In some embodiments, there is provided a device for inducing weight loss in a patient which includes a structure including an outer surface and an inner surface, a proximal end and a distal end, and a central portion, wherein the proximal end of the structure is sized to fit within an esophagus, wherein the distal end is sized to fit within a small intestine, and wherein at least a portion of the structure is impermeable or semi-permeable to stomach fluids.

In other embodiments, there is provided a device for inducing weight loss in a patient including:
 (i) at least one inner structure including a membrane which is impermeable or semi-permeable to gastric secretions; and
 (ii) at least one outer structure which is permeable to gastric secretions.

In still other embodiments, there is provided a device for inducing weight loss in a patient including:
 (i) at least one first panel including a proximal end and a distal end;
 (ii) at least one second panel including a proximal end and a distal end; and
 (iii) a channel therebetween;
 wherein said proximal end of said first panel is aligned with said proximal end of said second panel to form a portion suitable for insertion in an esophagus; and
 wherein said distal end of said first panel is aligned with said second end of said second panel to form a portion suitable for insertion in a small intestine.

In yet other embodiments, there is provided a method for inducing weight loss in a patient which includes the steps of:
 (i) inserting a structure including an outer surface and an inner surface, a proximal end and a distal end, and a central portion in the stomach of a patient,
 (ii) positioning the tubular structure within the stomach such that the proximal end of the tubular structure is positioned within an esophagus which leads to said stomach and such that the distal end of the tubular structure is positioned within a small intestine, wherein the proximal end of the structure is sized to fit within the esophagus, wherein the distal end of the structure is sized to fit within a small intestine, and wherein at least a portion of the structure is impermeable or semi-permeable to stomach fluids.

In still other embodiments, there is provided a method for inducing weight loss in patient which includes the step of inserting a device within the stomach of a patient, wherein the device includes:
  (i) at least one inner structure including a membrane which is impermeable or semi-permeable to gastric secretions; and
  (ii) at least one outer structure which is permeable to gastric secretions.

In yet other embodiments, there is provided a method for inducing weight loss in a patient which includes the steps of:
  (a) inserting a device within the stomach of a patient, wherein the device includes:
    (i) at least one first panel including a proximal end and a distal end;
    (ii) at least one second panel including a proximal end and a distal end; and
    (iii) a channel therebetween;
  wherein the proximal end of the first panel is aligned with the proximal end of the second panel to form a portion suitable for insertion in an esophagus; and
  wherein the distal end of the first panel is aligned with the second end of the second panel to form a portion suitable for insertion in a small intestine;
  (b) positioning the portion suitable for insertion in an esophagus within the esophagus of the patient; and
  (c) positioning the portion suitable for insertion in a small intestine within the small intestine of the patient.

In still other embodiments, there is provided a method for inducing weight loss in a patient including the steps of:
  (i) inserting a tubular structure having an outer surface and an inner surface, a proximal end and a distal end, and a central portion within a stomach of a patient;
  (ii) positioning the tubular structure within the stomach such that the proximal end of the tubular structure is positioned within an esophagus which leads to the stomach;
  (iii) passing the central portion and the distal portion of the tubular structure through a wall of the stomach such that the central portion of the tubular structure transverses the stomach from the esophagus to a small intestine external to the stomach; and
  (iv) re-inserting the distal portion of the tubular structure through a wall of a small intestine such that the distal portion of the tubular structure is positioned within a small intestine which receives digestive fluids flowing from the stomach.

In yet other embodiments, there is provided a method for inducing weight loss in a patient including the steps of:
  (i) placing at least one restrictive device in the esophagus of a patient;
  (ii) placing a device having an outer surface and an inner surface, a proximal end and a distal end, and a central portion into the gastrointestinal system of the patient, and
  (iii) positioning the device within the gastrointestinal system such that the proximal end of the device is positioned within the esophagus, such that the distal end of the device is positioned within the small intestine, and such that the central portion of the device transverses the stomach external to the stomach.

DETAILED DESCRIPTION OF THE INVENTION

This invention provides devices and methods for inducing weight loss. In some embodiments, the devices and methods of the present invention simulate gastric bypass surgery. In particular, the devices and methods of the present invention work to induce weight loss by limiting the intake and/or absorption of ingested food.

In some embodiments the devices and methods of the present invention work to induce weight loss by partially or completely closing off portions of the digestive system. In particular, in some embodiments, a device of the present invention is placed in the stomach such that the device transverses the stomach from the esophagus to the small intestine, thereby partially or completely closing off portions of the stomach and thereby reducing the volume of food which the stomach is capable of holding. As a result, weight loss is induced. In particular, an individual who has such a device in his or her stomach which closes off a portion of the stomach will feel satiated upon eating a smaller portion size. Consequently, such an individual has a greater likelihood of losing weight than an individual who does not have such a device in his or her stomach.

Moreover, in some embodiments, the devices and methods of the present invention eliminate digestion in the stomach by preventing the mixing of ingested food with gastric fluids or reduce digestion in the stomach by reducing the mixing of ingested food with gastric fluids. As a result of the elimination or reduction of digestion in the stomach, weight loss is induced. In particular, an individual who has a device of the present invention in his or her stomach which prevents or reduces digestion has a greater likelihood of losing weight than an individual who does not have such a device in his or her stomach.

In yet other embodiments, the devices and methods of the present invention provide a means to bypass portions of the digestive system where digestion occurs and/or a means to bypass portions of the digestive system where absorption of the products of digestion occurs. Specifically, in some embodiments, the devices and methods of the present invention provide a means to bypass the stomach and/or the upper duodenum of the small intestine. As a result, the amount of digestion and/or the amount of reabsorption of the byproducts of digestion is reduced, thereby inducing weight loss. In particular, an individual who has a device of the present invention which bypasses portions of the digestive system in his or her digestive system has a greater likelihood of losing weight than an individual who does not have such a device in his or her stomach.

These and other features of the invention will be more fully understood from the following description of specific embodiments of the invention taken together with the accompanying drawings. Unless otherwise defined herein, it should be noted that references herein to the term "distal" are to a direction towards the distal end of the duodenum, while references to the term "proximal" are to a direction towards the proximal end of the duodenum.

Figure 2:
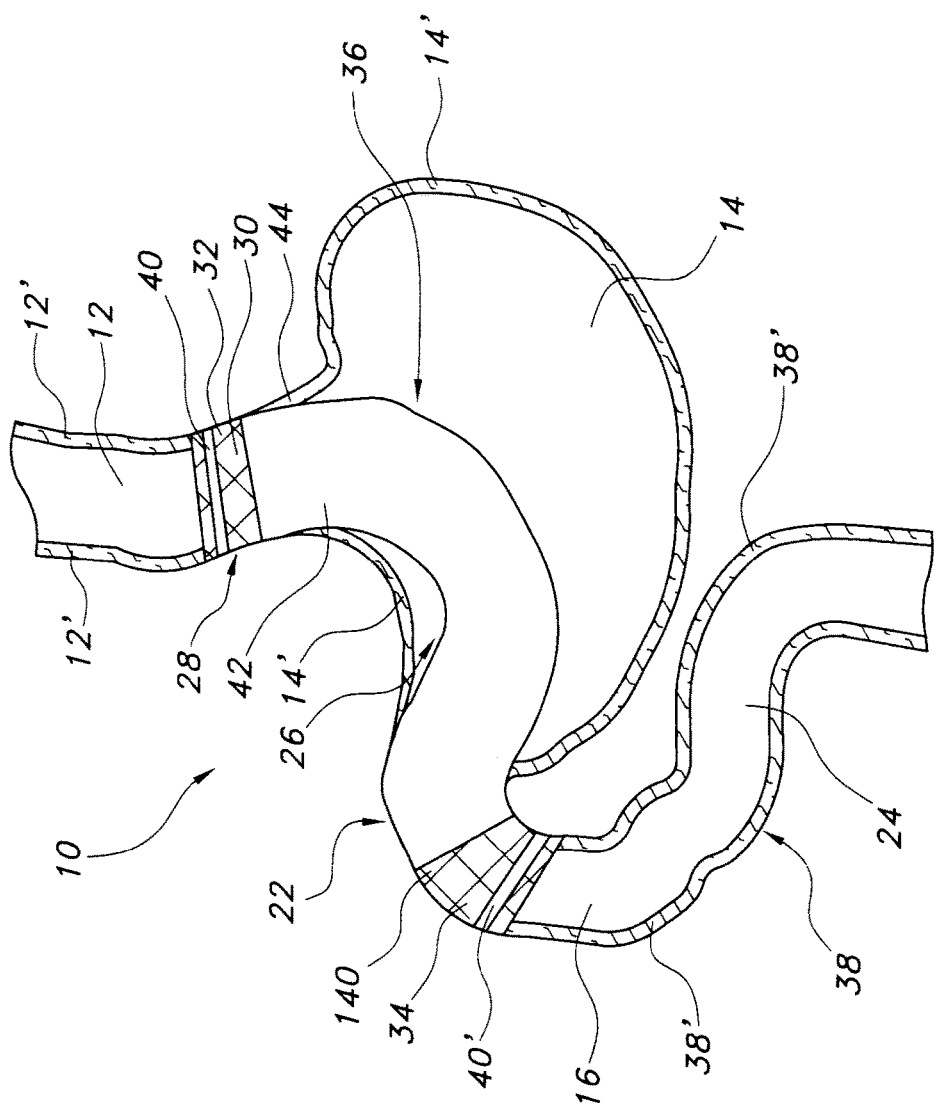
FIG. 2 is an anatomical elevational view of a stomach and adjacent esophagus and small intestine, the wall of the stomach, esophagus, and small intestine being broken away to show an anti-obesity device which is substantially covered with a coating layer over a substantial portion of the anti-obesity device in accordance with the present invention.

Referring to the drawings and, more particularly, to the anatomical elevational views of FIGS. 1 and 2, a central portion of alimentary canal 10 is illustrated in which device 26 of the present invention is located. This portion of the alimentary canal 10 includes distal end 44 of esophagus 12, stomach 14, and duodenum 16. Duodenum 16 is the proximate segment of the small intestine 38 relative to stomach 14, and has a proximal end 22 and a distal end 24 as shown in FIGS. 1 and 2. Esophagus 12 has an inner wall 12', stomach 14 has an inner wall 14', and small intestine 38 has an inner wall 38', as shown, for example, in FIGS. 1 to 3.

In one embodiment of the invention, a method of inducing weight loss in a patient includes inserting device 26 of the present invention in alimentary canal 10 and, more particularly, in stomach 14. In some embodiments, device 26 is a tubular structure 28 as shown in FIGS. 1 and 2. As further shown in FIG. 1, tubular structure 28 has an outer surface 30, a proximal end 32, a distal end 34, and a central portion 36. Desirably, proximal end 32 of tubular structure 28 is sized to fit within distal end 44 of esophagus 12 and distal end 34 of tubular structure 28 is sized to fit within small intestine 38 and, more particularly, within proximal end 22 of duodenum 16.

In accordance with a method of the present invention, tubular structure 28 is desirably positioned within stomach 14 such that proximal end 32 of tubular structure 28 is positioned within distal end 44 of esophagus 12, such that distal end 34 of tubular structure 28 is positioned within small intestine 38 and, more particularly, within proximal end 22 of duodenum 16, and such that central portion 36 transverses stomach 14 from esophagus 12 to small intestine 38 and, more particularly, to duodenum 16, as shown in FIGS. 1 and 2. Desirably, tubular structure 28 extends from at least pylorus 168 of stomach 14 to the duodenum 16 of small intestine 38, and more desirably from the distal end 44 of the esophagus 12 to the pylorus 168 or beyond, as shown, for example, in FIG. 1. The device 26 may include visual markers (not shown) at the proximal end 32 to aid in the placement of the device 26 at the distal end 44 of the esophagus 12. Alternatively, or in addition to, visual markers (not shown) may be placed by a practitioner to note a transition from esophagus cells to stomach cells to aid in the placement of the proximal end 32 of the device 26 thereat.

Figure 3:
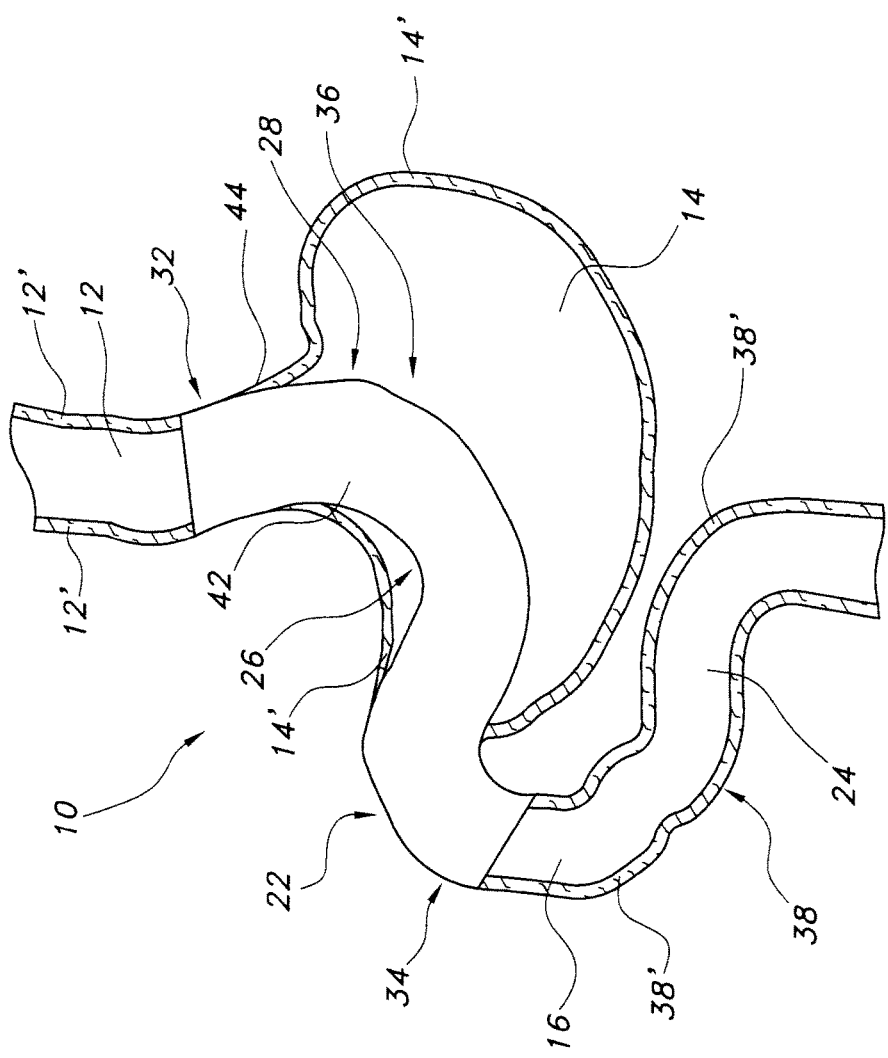
FIG. 3 is an anatomical elevational view of a stomach and adjacent esophagus and small intestine, the wall of the stomach, esophagus, and small intestine being broken away to show an anti-obesity device which is entirely covered with a coating layer in accordance with the present invention.

In some embodiments, tubular structure 28 is impermeable or semi-permeable to fluids within stomach 14. In other embodiments, device 26 includes a coating layer 42 which renders device 26 impermeable or semi-permeable to fluids within stomach 14. In particular, in some embodiments, device 26 may include a coating layer 42 which covers at least a portion of tubular structure 28. In some embodiments, coating layer 42 substantially covers tubular structure 28, as shown in FIG. 2. Desirably, coating layer 42 entirely covers tubular structure 28, as shown in FIG. 3. Permeability may be a characteristic of the coating layer 42 and/or may be part of the structural design of the device 26 by, for example, placing holes through the coating layer 42.

Accordingly, in some embodiments, the method of the present invention includes placing a coating layer 42 over at least a portion of device 26 and, more particularly, over a portion of tubular structure 28. Specifically, in some embodiments, the method of the present invention includes placing a coating layer 42 over tubular structure 28 such that coating layer 42 substantially or entirely covers tubular structure 28.

In some embodiments, device 26 includes at least one retainer structure 40, as shown in FIG. 2. Retainer structure 40 may be a part of device 26 or may be a separate structure which is connected to device 26.

In some embodiments, a retainer structure 40 secures proximal end 32 of tubular structure 28 within esophagus 12, and more particularly, within distal end 44 of esophagus 12. In such embodiments, retainer structure 40 desirably provides resistance to axial displacement of device 26 and, more particularly, tubular structure 28, within esophagus 12.

Moreover, in some embodiments, a retainer structure 40' secures distal end 34 of tubular structure 28 within small intestine 38 and, more particularly, within proximal end 22 of duodenum 16. In such embodiments, retainer structure 40' desirably provides resistance to axial displacement of device 26 and, more particularly, tubular structure 28, within small intestine 38 and, more particularly, within proximal end 22 of duodenum 16.

In some embodiments, two or more retainer structures 40, 40' are used to secure tubular structure 28 within stomach 14 such that central portion 36 of tubular device 28 transverses stomach 14 from distal end 44 of esophagus 12 to small intestine 38. In particular, in some embodiments retainer structure 40 secures the proximal end 32 of tubular structure 28 within esophagus 12 and, more particularly, within distal end 44 of esophagus 12, and another retainer structure 40' secures distal end 34 of tubular structure 28 within small intestine 38 and, more particularly, within proximal end 22 of duodenum 16, as shown in FIG. 2.

Accordingly, in some embodiments, the method of the present invention includes securing the proximal end 32 of tubular structure 28 within esophagus 12 and, more particularly, within distal end 44 of esophagus 12 by means of at least one retainer structure 40 and/or securing distal end 34 of tubular structure 28 within small intestine 38 and, more particularly, within duodenum 16 by means of at least one retainer structure 40'. Thus, in some embodiments, the method of the present invention includes the step of positioning at least one retainer structure 40 within the proximal end 32 of tubular structure 28 to secure proximal end 32 of tubular structure within esophagus 12 and, more particularly, within distal end 44 of esophagus 12. Alternatively, or in addition, in some embodiments, the method of the present invention includes the step of positioning at least one retainer structure 40' within distal end 34 of tubular structure 28 to secure distal end 34 of tubular structure 28 within small intestine 38 and, more particularly, within proximal end 22 of duodenum 16.

Retainer structures 40, 40' may be any suitable retainer structure known in the art. In some embodiments, retainer structures 40, 40' are annular rings as show in FIGS. 2, 5, and 6A-6B.

Figure 18:
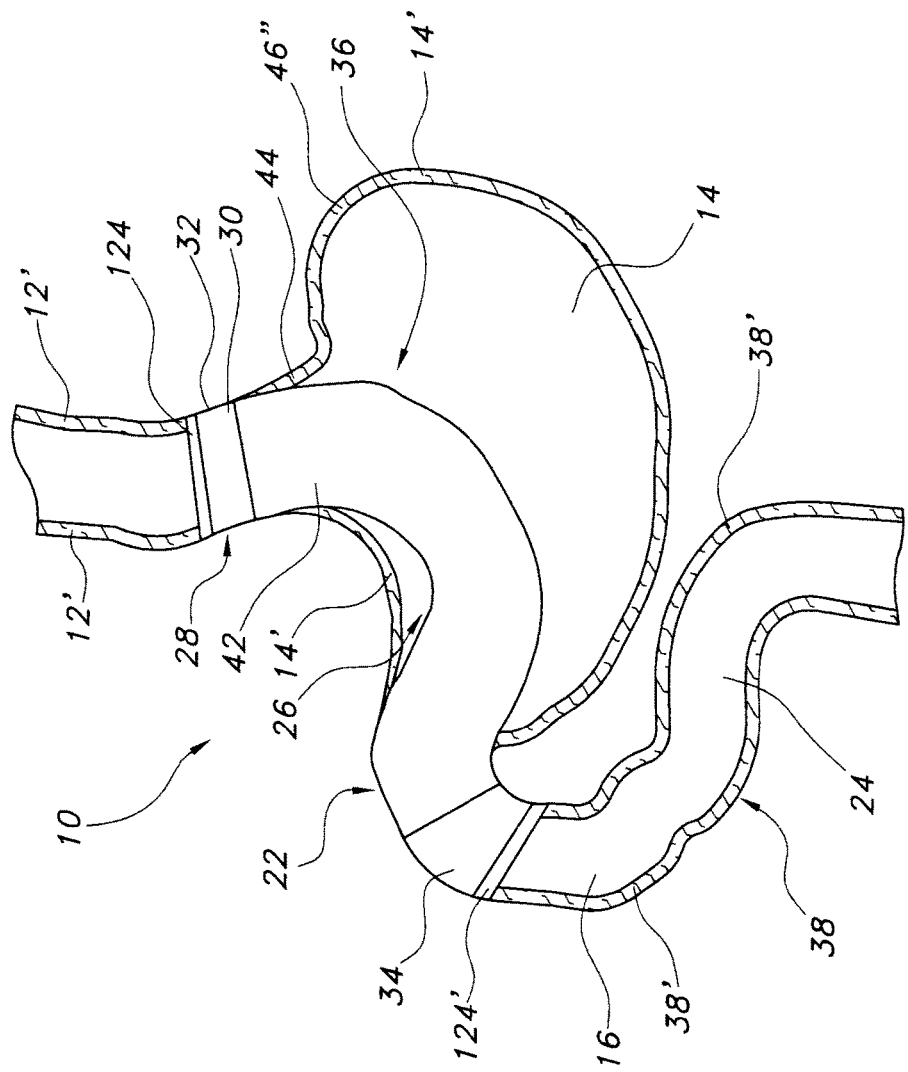
FIGS. 18-24 are anatomical elevational views of a stomach and adjacent esophagus and small intestine, the wall of the stomach, esophagus, and small intestine being broken away to show an anti-obesity device which includes various retainer structures and which is substantially covered with a coating layer over a substantial portion of the anti-obesity device in accordance with the present invention.

In other embodiments, retainer structure 40 may be a circumferential groove 124 which is formed on the outer surface 30 of device 26 and, more particularly, on the outer surface of proximal end 32 of tubular structure 28, as shown in FIG. 18. In such embodiments, inner surface 12' of distal end 44 of esophagus 12 extends into the circumferential groove to provide resistance to axial displacement of device 26 within esophagus 12 and, more particularly, to provide resistance to axial displacement of tubular structure 28 within distal end of esophagus 44. Such a circumferential groove is desirably transverse relative to device 26 and, more particularly, to tubular structure 28, and may be circular.

Additionally, or in the alternative, in some embodiments, retainer structure 40' may be a circumferential groove 124' which is formed on the outer surface 30 of device 26 and, more particularly, on the outer surface 30 of distal end 34 of tubular structure 28, as further shown in FIG. 18. In such embodiments, inner surface 38' of proximal end 32 of small intestine 38 and, more particularly, inner surface 38' of duodenum 16 extends into the circumferential groove to provide resistance to axial displacement of device 26 within small intestine 38 and, more particularly, to axial displacement of tubular structure 28 within proximal end 22 of duodenum 16. Such a circumferential groove is transverse relative to device 26 and, more particularly, tubular structure 28, and may be circular.

Figure 19:
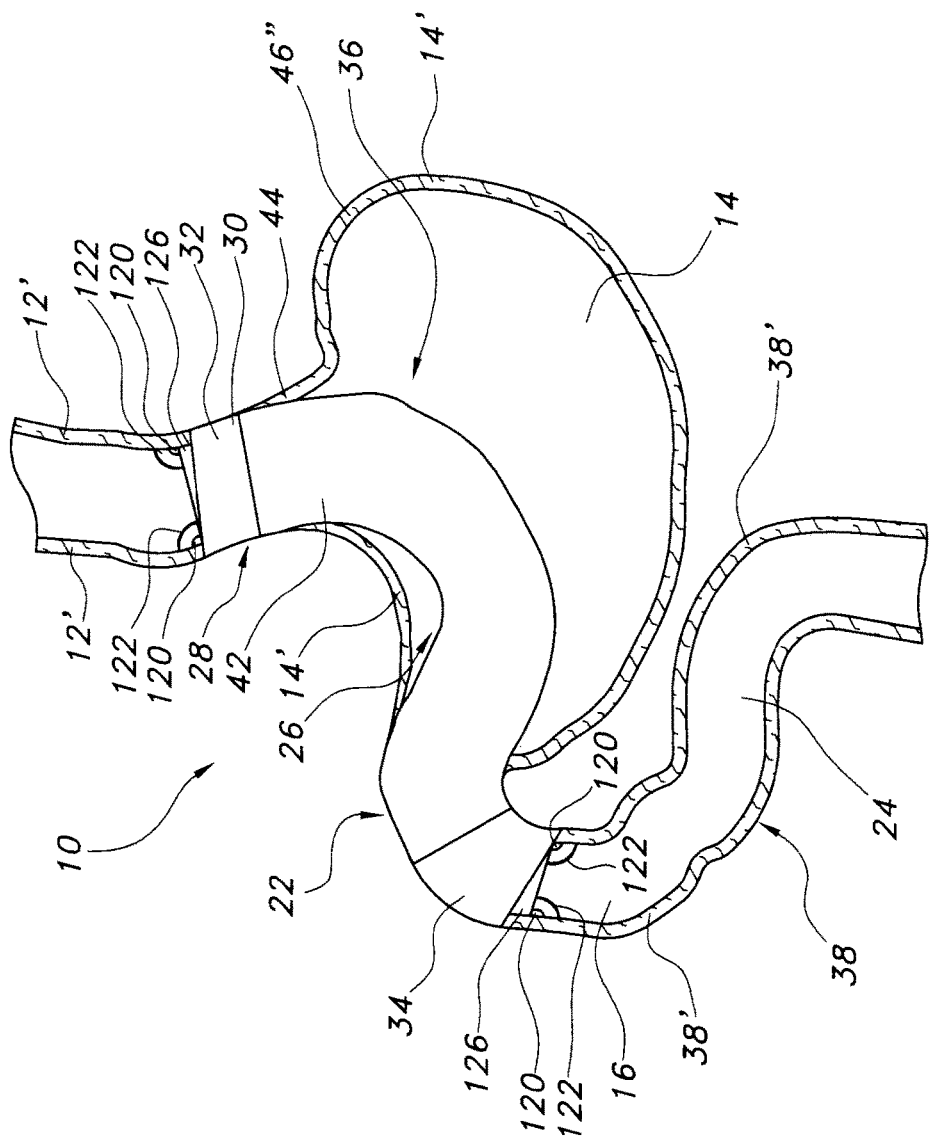

In yet other embodiments, retainer structures 40, 40' may be a protuberance 126, 126' which extends from the outer surface of device 26 and, more particularly, tubular structure 28, as shown in FIG. 19. The protuberance may include hooks and pins 120 which have a distal end which is pointed and may include one or more barbs 122.

Desirably, when retainer structure 40 is a protuberance, the protuberance has an outer surface and a radial dimension such that the outer surface of the protuberance engages the inner surface 12' of esophagus 12 when device 26, and more particularly, proximal end 32 of tubular structure 28 is positioned within distal end 44 of esophagus 12, thereby anchoring device 26 and, more particularly, tubular structure 28, to distal end 44 of esophagus 12.

Additionally, or in the alternative, when retainer structure 40' is a protuberance, the protuberance has an outer surface and a radial dimension such that the outer surface of the protuberance engages the inner surface 38' of small intestine 38 and, more particularly, the proximal end 22 of duodenum 16, thereby anchoring device 26 and, more particularly, tubular structure 28 to proximal end 22 of duodenum 16.

Figure 20:
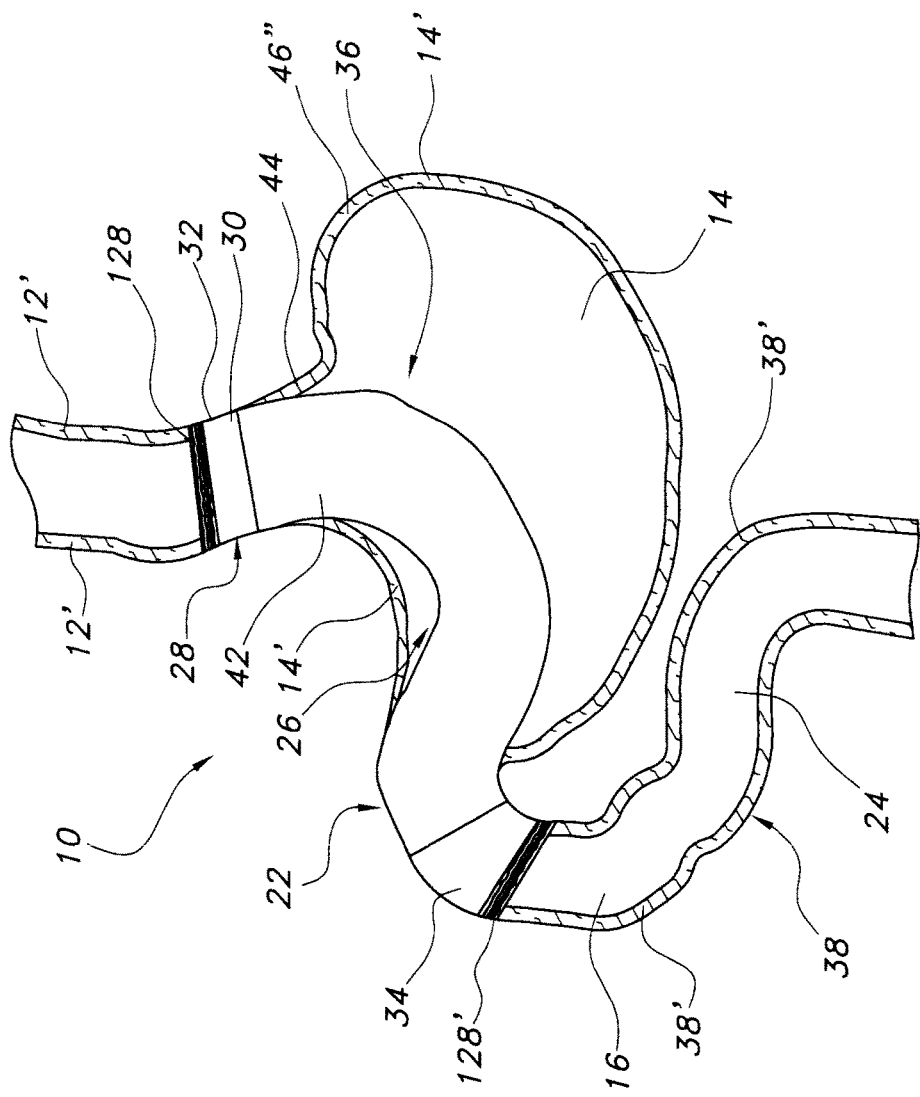

In other embodiments, retainer structures 40, 40' may include one or more sections 128, 128' which are roughened or knurled, as shown in FIG. 20. Desirably, roughened or knurled section of retainer structure 40 engages the inner surface 12' of esophagus 12 when device 26, and more particularly, proximal end 32 of tubular structure 28 is positioned within distal end 44 of esophagus 12, thereby anchoring device 26 and, more particularly, tubular structure 28, to distal end 44 of esophagus 12. Desirably, roughed or knurled section 128' of retainer structure 40' engages the inner surface 38' of small intestine 38 and, more particularly, the proximal end 22 of duodenum 16, thereby anchoring device 26 and, more particularly, tubular structure 28, to proximal end 22 of duodenum 16.

Figure 21:
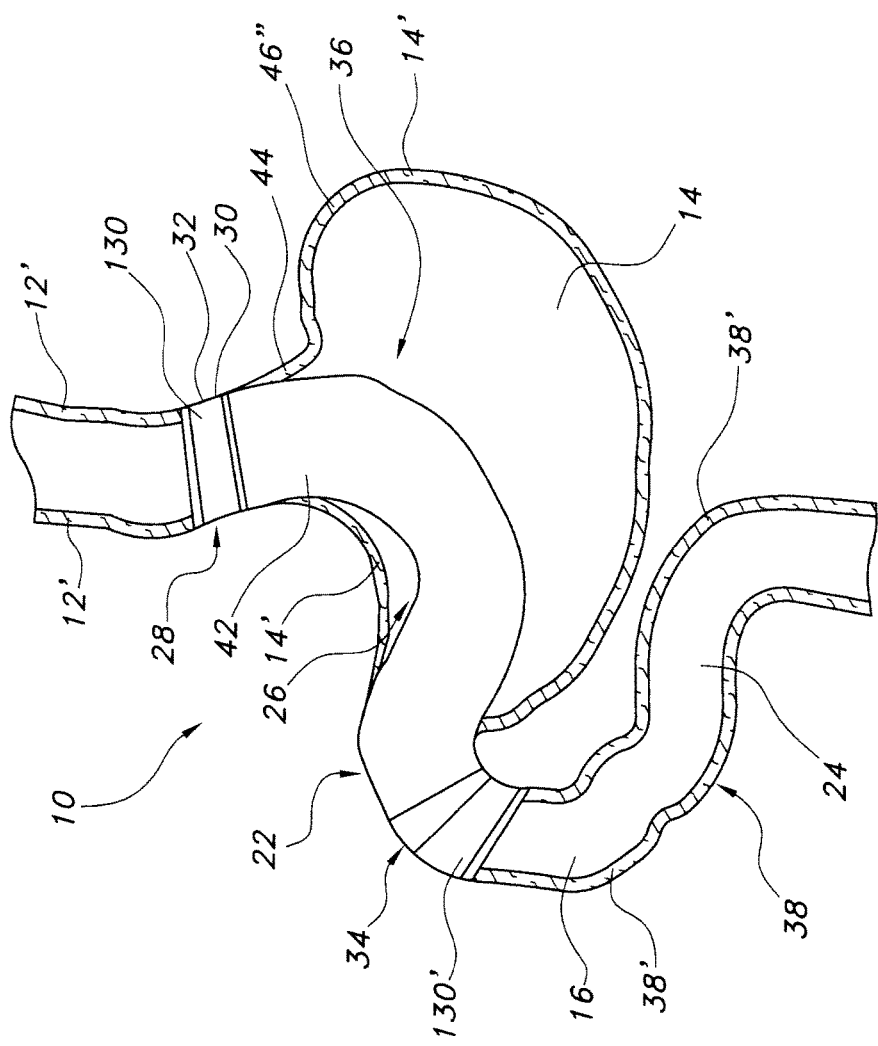

In some embodiments, retainer structures 40, 40' are semi-rigid bands 130, 130' secured to device 26 and, more particularly, tubular structure 28, as shown in FIG. 21. Where retainer structure 40 is a semi-rigid band 130, the semi-rigid band 130 is transversely expandable to one or more outer diameters which are sufficiently large to anchor the proximal end 32 of tubular structure 28 to the inner surface 12' of distal end of esophagus 44. Likewise, where tubular structure 40' is a semi-rigid band 130', the semi-rigid band is transversely expandable to one or more outer diameters which are sufficiently large to anchor the distal end 34 of tubular structure 28 to the inner wall 38' of proximal end 22 of duodenum 16. The semi-rigid band may have a ratcheting mechanism which provides for the transverse expansion of the band. The semi-rigid band may include polymeric material or metal.

Figure 21A:
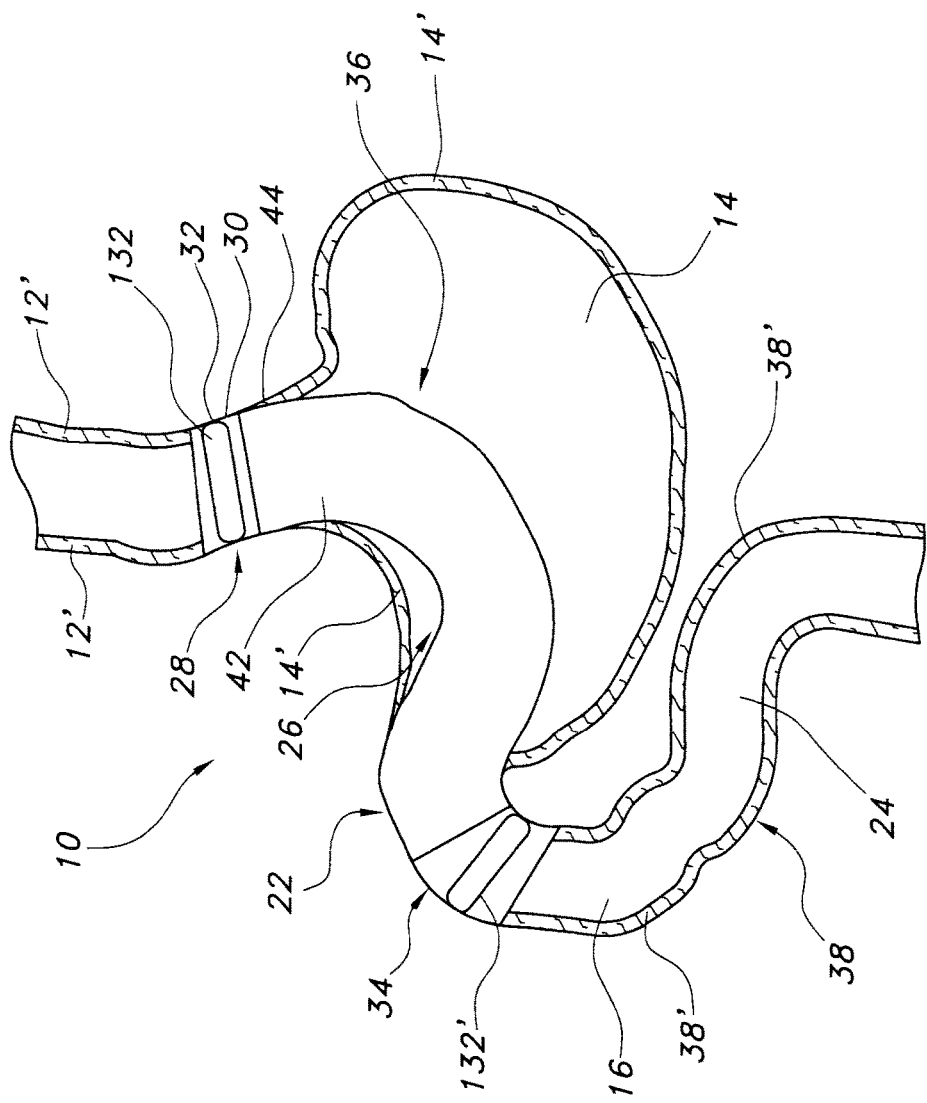

In still other embodiments, retainer structures 40, 40' include one or more elongate anchor members 132, 132' which are secured to device 26 and, more particularly, to tubular structure 28, as shown in FIG. 21A. Each anchor member is arcuate, and has a transverse orientation relative to device 26 and, more particularly, to tubular structure 28. The arcuate extent of the anchor members may be 300 degrees. Where the retainer structure 40 is an anchor member 132, retainer structure 40 extends radially outward from the outer surface 30 of device 26 and, more particularly, radially outward from tubular structure 28, a sufficient distance to anchor the device 26 and, more particularly, tubular structure 28 to the inner wall 12' of the distal end 44 of esophagus 12. Where the retainer structure 40' is an anchor member 132', retainer structure 40' extends radially outward from the outer surface 30 of device 26 and, more particularly, from the outer surface 30 of tubular structure 28, to the inner wall 38' of small intestine 38 and, more particularly, to the inner surface 38' of proximal end 22 of duodenum 16. Retainer structures 40, 40' may include, but are not limited to, fasteners, for example T-shaped fasteners, button-type fasteners, clips, clamps and the like, individually or in combination.

Figure 22:
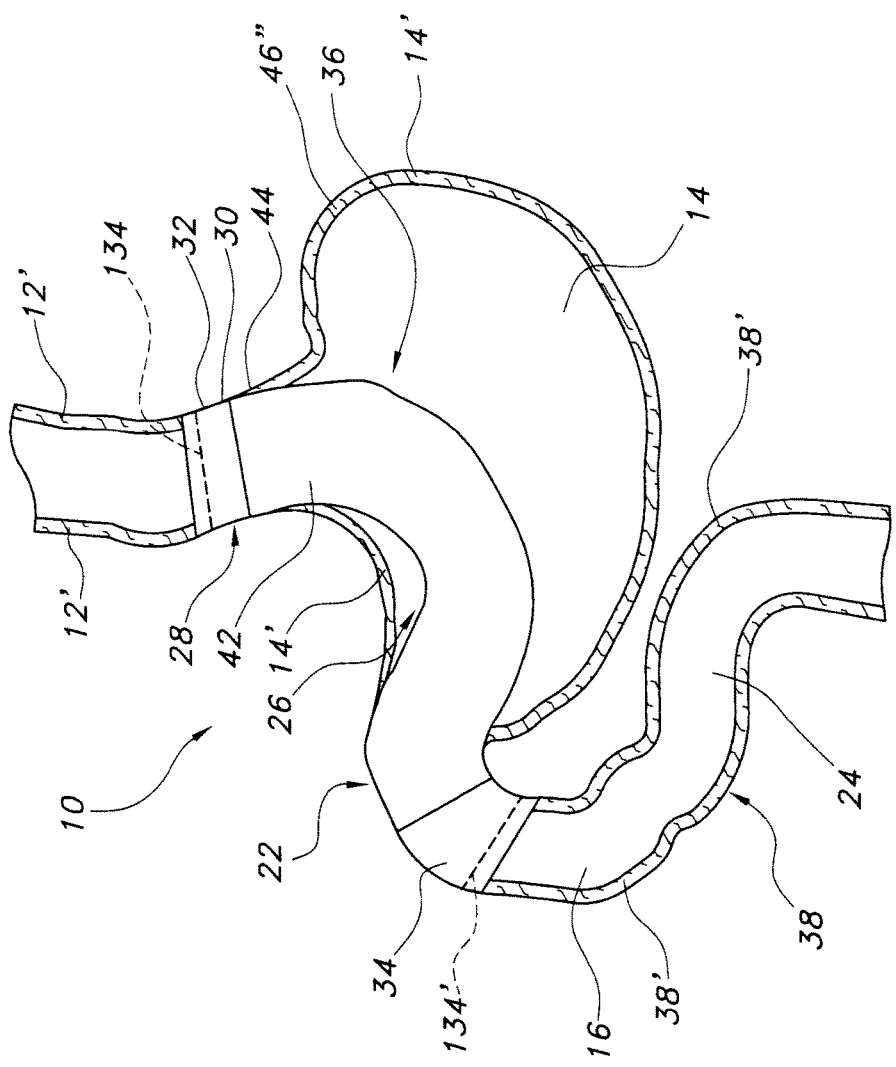

In yet other embodiments, retainer structures 40, 40' may be sutures 134, 134', as shown in FIG. 22. Where the retainer structure 40 is a suture 134, retainer structure 40 anchors device 26 and, more particularly, tubular structure 28 to the inner wall 12' of the distal end 44 of esophagus 12. In such embodiments, retainer structure 40 prevents axial and rotational displacement of device 26 and, more particularly, tubular structure 28 relative to the distal end 44 of esophagus 12. Where the retainer structure 40' is a suture 134', retainer structure 40' anchors device 26 and, more particularly, the outer surface 30 of tubular structure 28, to the inner wall 38' of small intestine 38 and, more particularly, to the inner wall 38' of proximal end 22 of duodenum 16. In such embodiments, retainer structure 40' prevents axial and rotational displacement of device 26 and, more particularly, tubular structure 28 relative to the proximal end 22 of small intestine 38 and, more particularly, relative to the proximal end 22 of duodenum 16.

Figure 23:
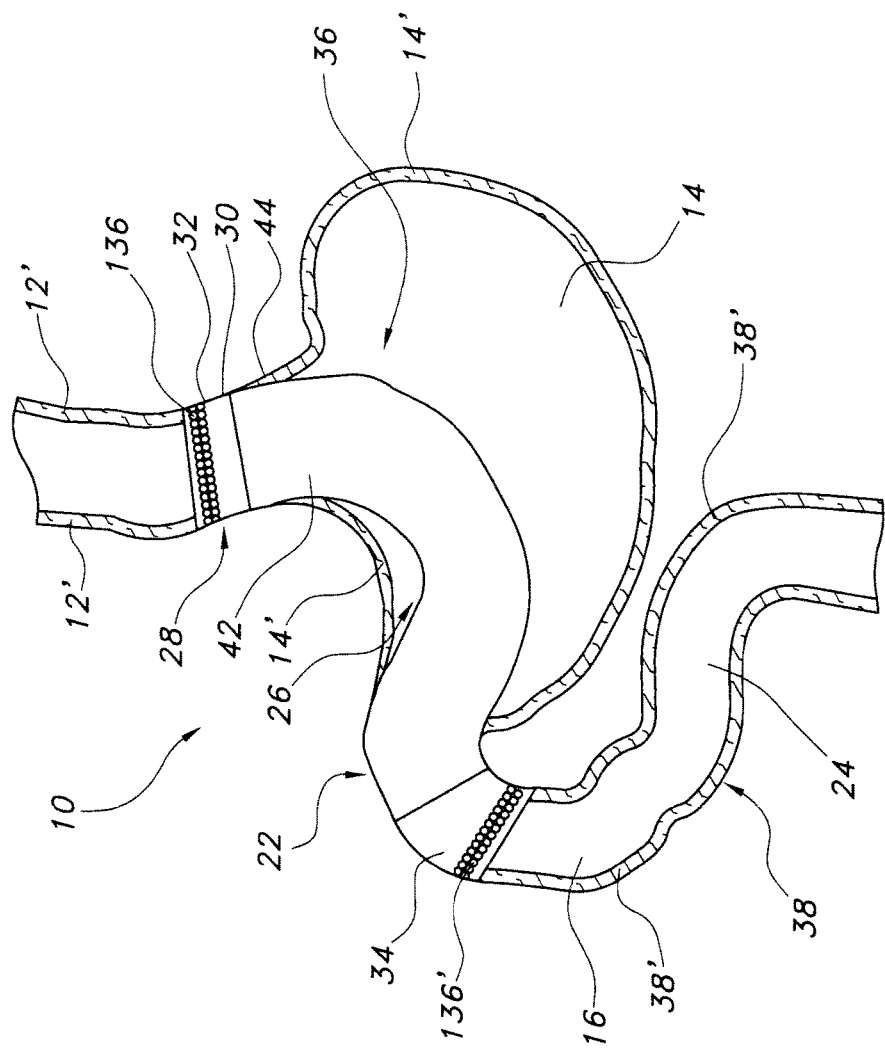

In still other embodiments, retainer structures 40, 40' may be an adhesive material or a structure which includes an adhesive material thereon 136, 136', as shown in FIG. 23. Where the retainer structure 40 is an adhesive material or a structure which includes an adhesive material 136 thereon, adhesive material 136 anchors the outer surface 30 of device 26 and, more particularly, the outer surface 30 of tubular structure 28 to the inner surface 12' of the distal end 44 of esophagus 12. In such embodiments, retainer structure 40 prevents axial and rotational displacement of device 26 and, more particularly, tubular structure 28 relative to the distal end 44 of esophagus 12. Where retainer structure 40' is an adhesive material or a structure which includes an adhesive material 136', adhesive material 136' anchors outer surface 30 of device 26 and, more particularly, outer surface 30 of tubular structure 28, to the inner wall 38' of small intestine 38 and, more particularly, to the inner wall 38' of proximal end 22 of duodenum 16. In such embodiments, retainer structure 40' prevents axial and rotational displacement of device 26 and, more particularly, tubular structure 28 relative to the proximal end 22 of small intestine 38 and, more particularly, relative to the proximal end 22 of duodenum 16.

Figure 24:
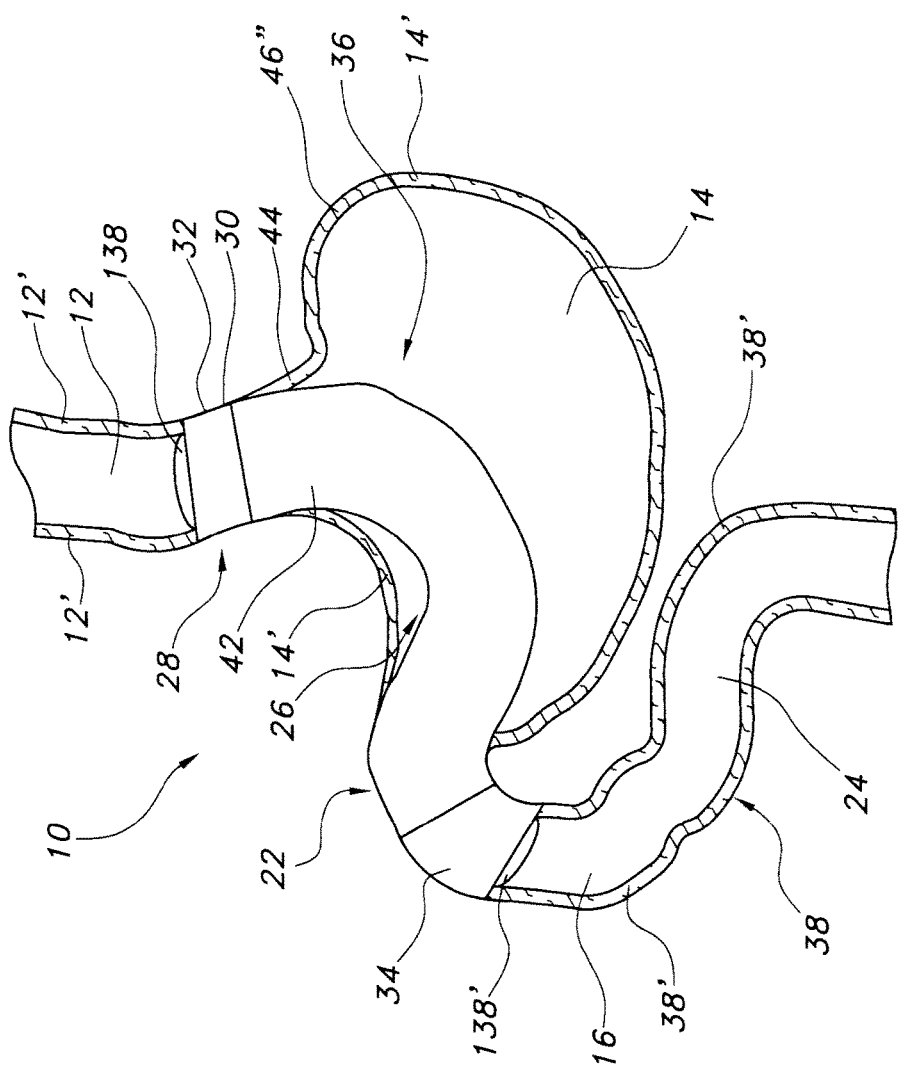

In other embodiments, retainer structures 40, 40' may be a balloon or sponge 138, 138' which is inserted into device 26 and, more particularly, into tubular structure 28, as shown in FIG. 24, after tubular structure 28 is positioned within stomach 14 in accordance with a method of the present invention. Balloon or sponge 138, 138' may be expanded to result in radial expansion of device 26 and, more particularly, tubular structure 28, to cause engagement of the outer surface 30 of device 26 and, more particularly, tubular structure 28, with the inner wall 12' of esophagus 12 and the inner wall 38' of small intestine 38. Desirably, as a result of the expansion of balloon or sponge 138, 138', device 26 and, more particularly, tubular structure 28, is anchored within the alimentary canal 10 such that the proximal end 32 of tubular device 26 and, more particularly, proximal end 32 of tubular structure 28 is secured within distal end 44 of esophagus 12 and such that distal end 34 of device 26 and, more particularly, distal end 34 of tubular structure 28 is secured within proximal end 22 of small intestine 38 and, more particularly, within proximal end 22 of duodenum 16.

Figure 4:
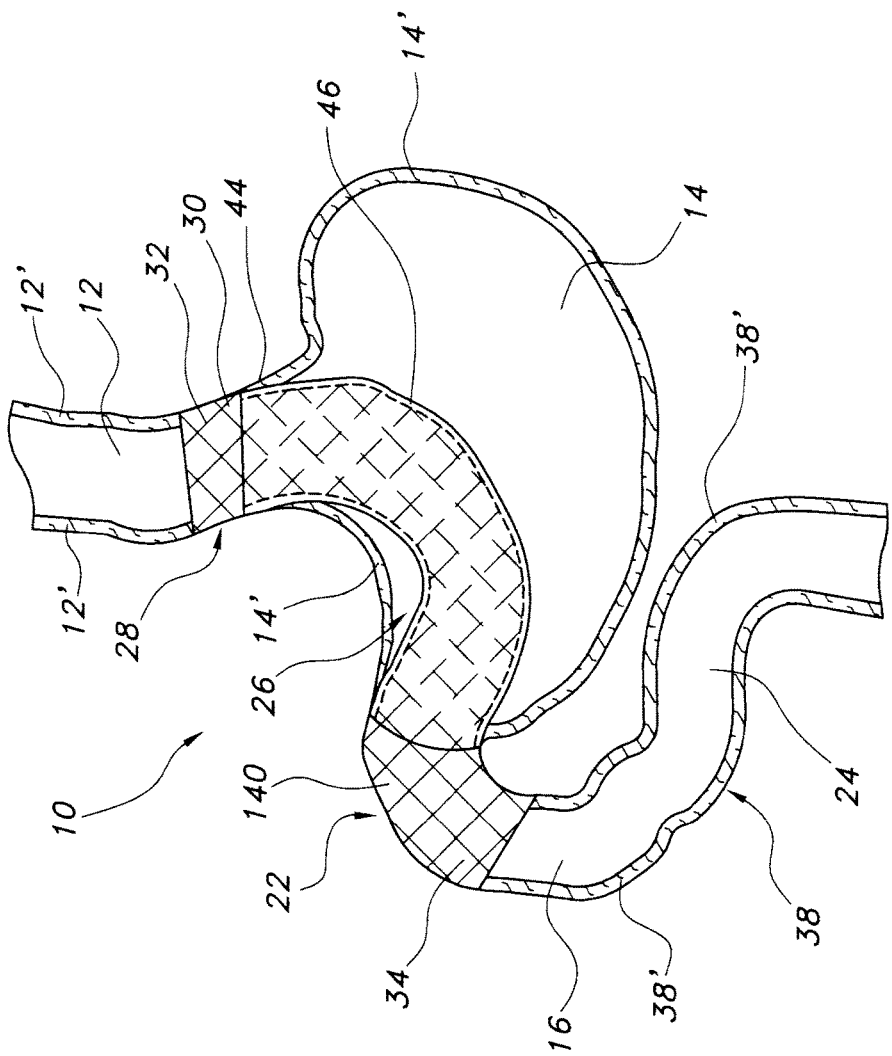
FIG. 4 is an anatomical elevational view of a stomach and adjacent esophagus and small intestine, the wall of the stomach, esophagus, and small intestine being broken away to show an anti-obesity device which is positioned within a stabilizing structure in accordance with the present invention.

In some embodiments, device 26 includes at least one structure 46 which is capable of expanding to fit within stomach 14, as shown in FIG. 4. In particular, in some embodiments, tubular structure 28 includes at least one structure 46 which is positioned about tubular structure 28 and which is capable of expanding to fit within stomach 14. Desirably, structure 46 is a stabilizing structure that expands to interact with the stomach wall 14' and limit displacement along the gastrointestinal tract, particularly alimentary canal 10. Accordingly, in some embodiments, the method of the present invention includes positioning a structure such as a stabilizing structure 46 over device 26 and, more particularly, over tubular structure 28. In such embodiments, stabilizing structure 46 expands to interact with inner wall 14' of stomach 14 to limit displacement of device 26 and, more particularly, to limit displacement of tubular structure 28, within alimentary canal 10 of the gastrointestinal tract. With reference to FIG. 4, portion of tubular structure 28 which is positioned under structure 46 is shown in hatch-marks.

Figure 5:
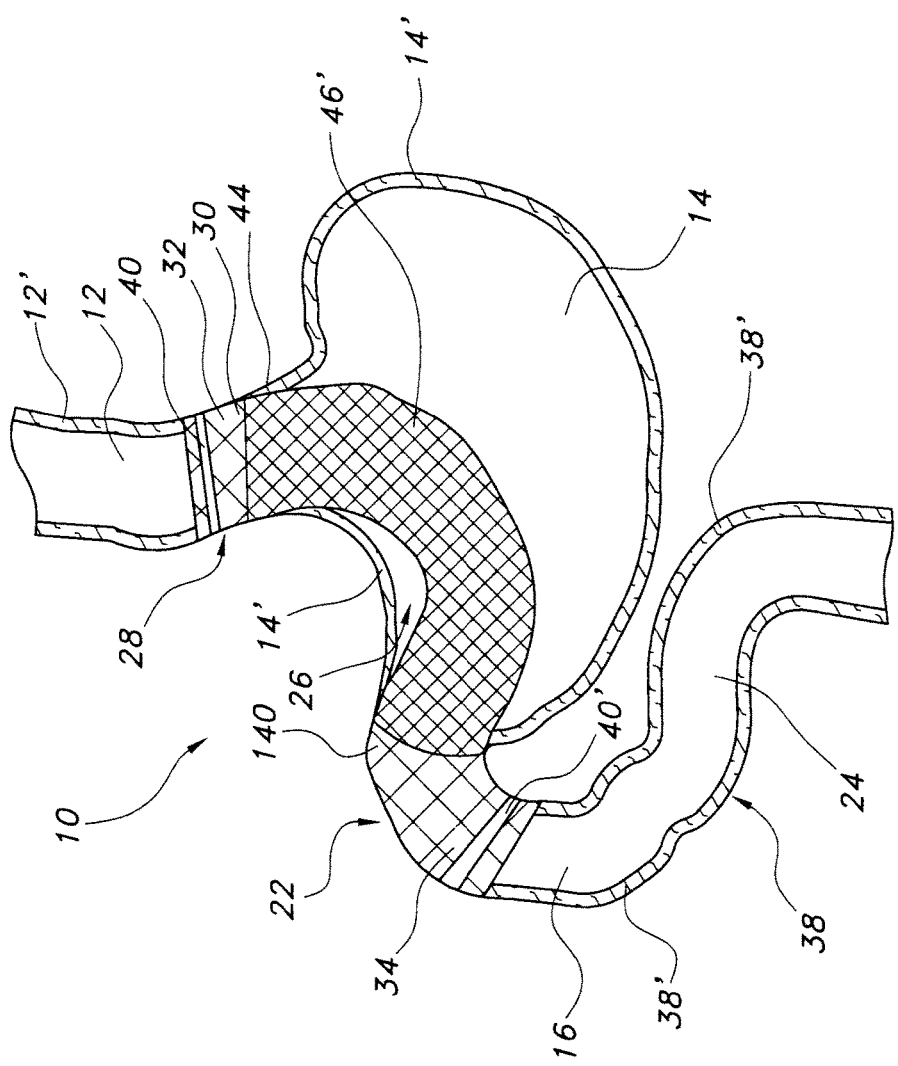
FIG. 5 is an anatomical elevational view of a stomach and adjacent esophagus and small intestine, the wall of the stomach, esophagus, and small intestine being broken away to show an anti-obesity device which is positioned within a mechanical expanding device in accordance with the present invention.

In some embodiments, structure 46 may be a mechanical expanding device 46', such as a stent, which is capable of expansion, as shown in FIG. 5. Stent may have any suitable configuration known in the art and as disclosed herein. Accordingly, in some embodiments, the method of the present invention includes positioning a stabilizing structure 46 such as a mechanical expanding device 46' and, more particularly, a stent which is capable of expansion, over device 26 and, more particularly, over tubular structure 28. Stabilizing structure 46 may be used alone or in conjunction with at least one retainer structure 40 to secure device 26 and, more particularly, tubular structure 28 within stomach 14. In some embodiments, structure 46 may be used in conjunction with at least two retainer structures 40, 40' as shown in FIG. 5. Although mechanical expanding device 46' is shown over only a portion of device 26 and, more particularly, over only a portion of tubular structure 28 in FIG. 5, it will be understood the mechanical expanding device 46' may cover device 26 and, more particularly, tubular structure 28, in its entirety.

Figure 6A:
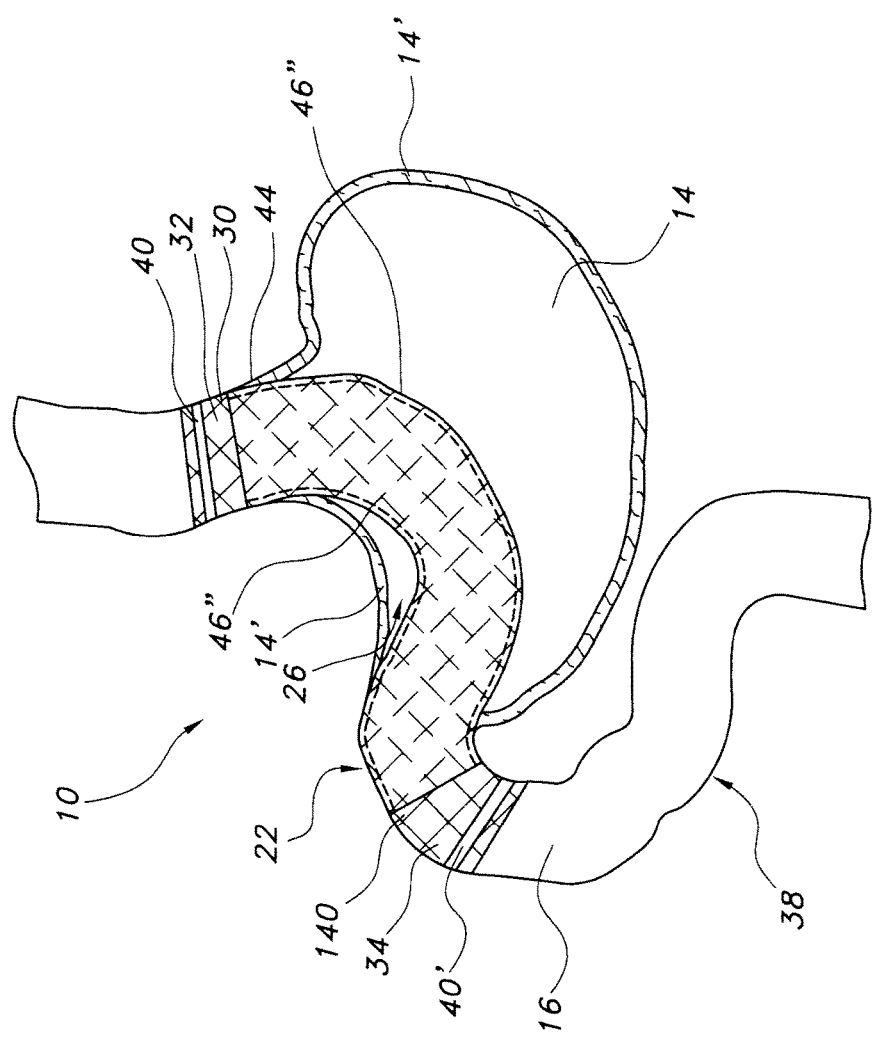
FIG. 6A is an anatomical elevational view of a stomach and adjacent esophagus and small intestine, the wall of the stomach, esophagus, and small intestine being broken away to show an anti-obesity device which is positioned within an inflatable structure in its uninflated stated in accordance with the present invention.
Figure 6B:
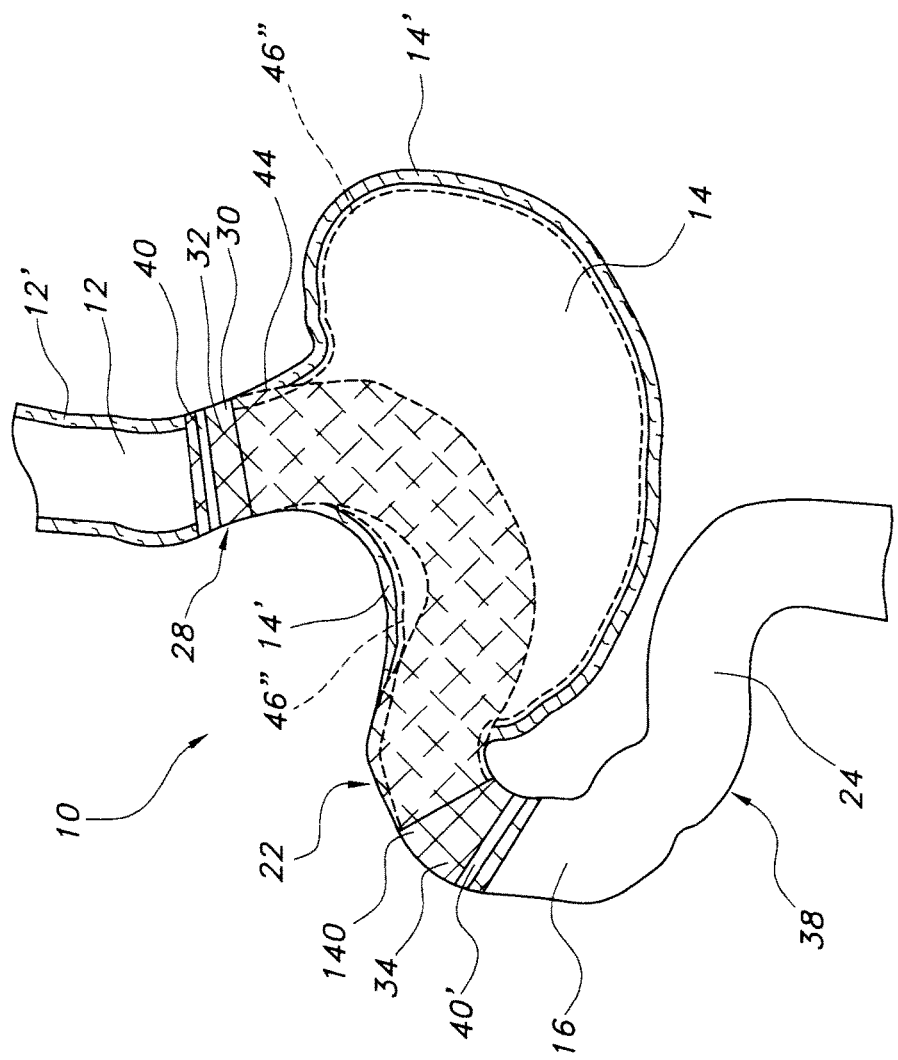
FIG. 6B is an anatomical elevational view of a stomach and adjacent esophagus and small intestine, the wall of the stomach, esophagus, and small intestine being broken away to show an anti-obesity device which is positioned within an inflatable structure in its inflated stated in accordance with the present invention.

In other embodiments, structure 46 may be an inflatable structure 46'', such as an anchoring balloon, which is capable of expanding to fit within stomach 14. Accordingly, in some embodiments, the method of the present invention includes positioning a structure 46 such as an inflatable structure 46'' over device 26 and, more particularly, over tubular structure 28 such that tubular structure 28, which may be a stent, is housed inside inflatable structure 46'', as shown in FIG. 6A in its uninflated state. In such embodiments, inflatable structure 46'' anchors tubular structure 28, which may be a stent, within stomach 14 upon inflation of inflatable structure 46'', as shown in FIG. 6B. Accordingly, in some embodiments, the method of the present invention includes inflating inflatable structure 46'' within stomach 14 such that inflatable structure 46'' anchors device 26 and, more particularly, tubular structure 28, which may be a stent, within stomach 14 as shown in FIG. 6B. With reference to FIGS. 6A and 6B, portion of tubular structure 28 which is positioned under structure 46 is shown in hatch-marks.

Inflatable structure 46'' may be made of any suitable material. Suitable materials for inflatable structure 46'' include, but are not limited to, for example, neoprene, urethane, silicone, polyethylene terephthalate and combinations thereof.

Figure 7:
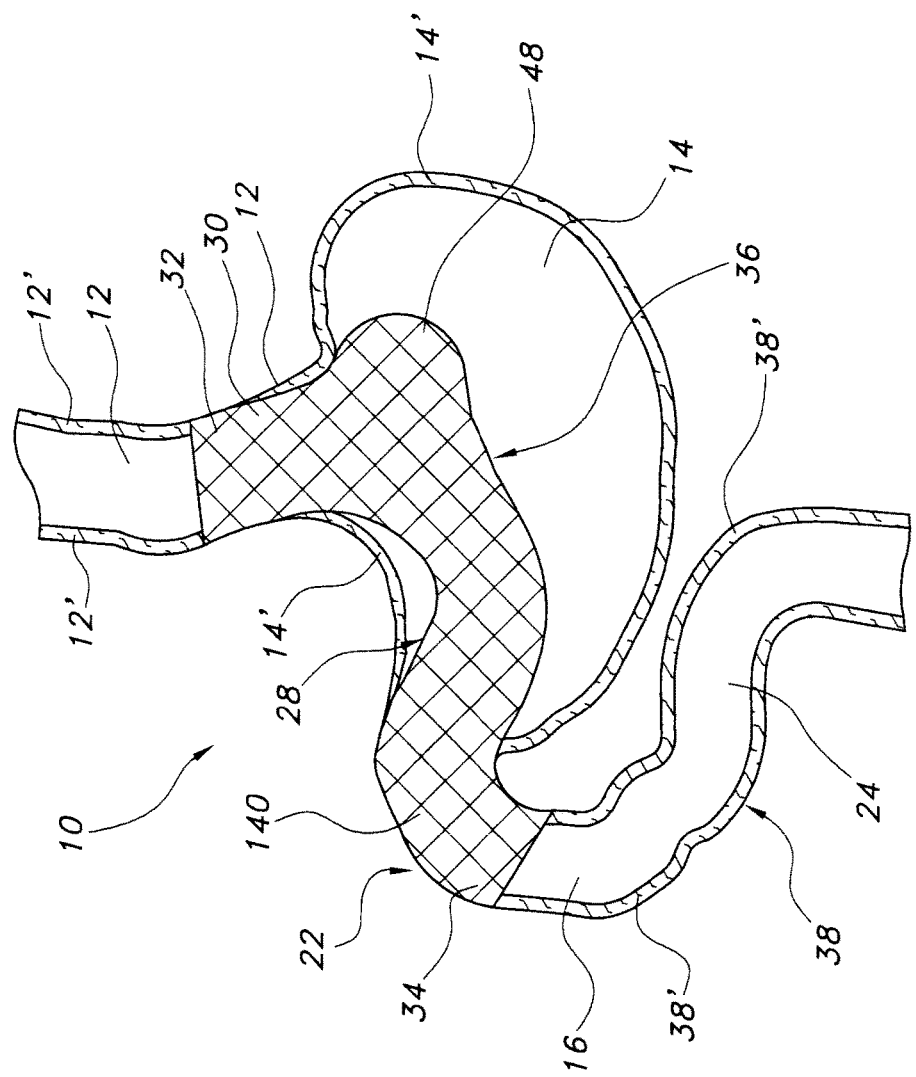
FIG. 7 is an anatomical elevational view of a stomach and adjacent esophagus and small intestine, the wall of the stomach, esophagus, and small intestine being broken away to show an anti-obesity device having an enlarged portion in accordance with the present invention.

In some embodiments, tubular structure 28 includes at least one enlarged area 48, as shown in FIG. 7. In some embodiments, enlarged area is a distensible portion 48, as shown in FIG. 7. In some embodiments, distensible portion 48 is a pouch as shown in FIG. 7. In particular, enlarged area acts as a pouch 48 which may store food for a period of time in stomach 14. Pouch 48 allows for digestion of food within stomach 14. Because pouch 48 is smaller in volume than stomach 14, lesser amounts of food are digested in stomach 14 and lesser amounts of the byproducts of digestion are subsequently reabsorbed in the small intestine 38, thereby inducing weight loss.

Figure 8:
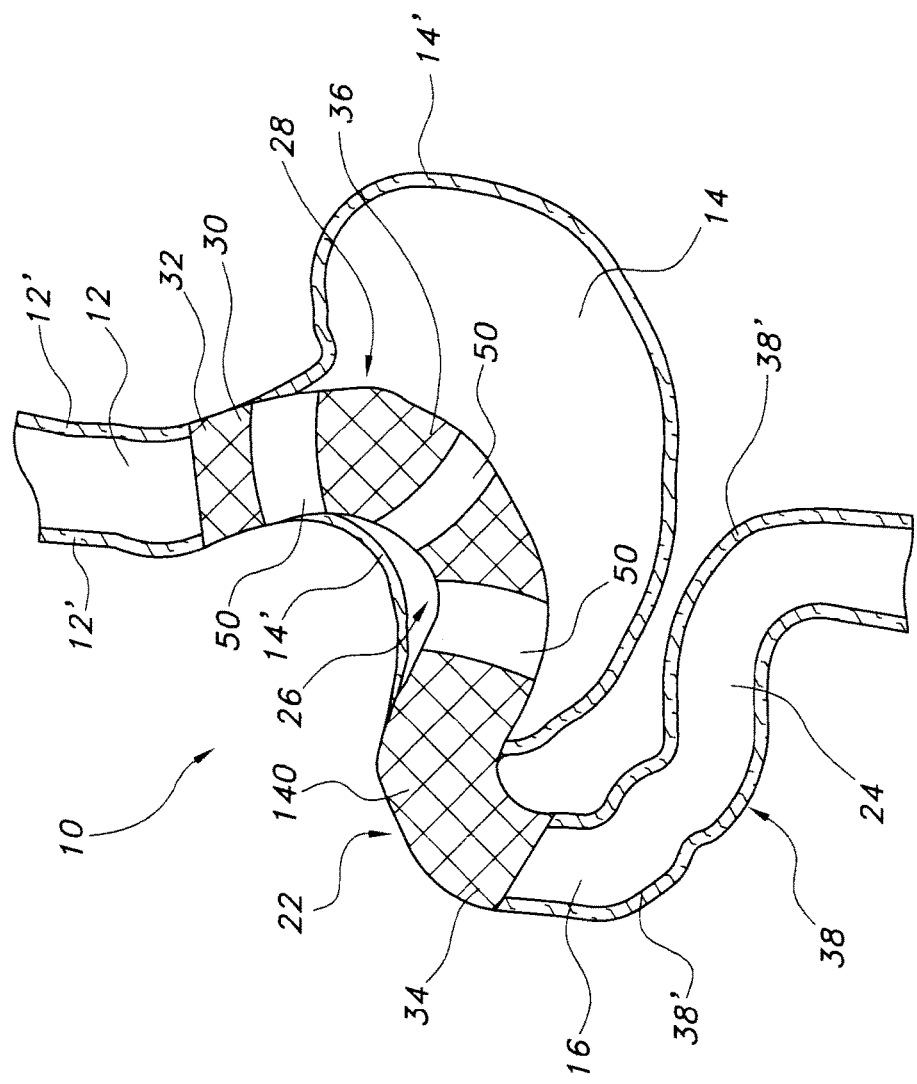
FIG. 8 is an anatomical elevational view of a stomach and adjacent esophagus and small intestine, the wall of the stomach, esophagus, and small intestine being broken away to show an anti-obesity device having adjustable bands in accordance with the present invention.

In some embodiments, device 26 includes at least one adjustable structure 50 which is positioned about device 26 as shown in FIG. 8. In particular, in some embodiments, tubular structure 28 includes at least one adjustable structure 50 which is positioned about tubular structure 28. Desirably, adjustable structure 50 is an adjustable band, as shown in FIG. 8. In particular, in some embodiments, the method of the present invention includes positioning at least one adjustable band 50 about device 26 and, more particularly, about tubular structure 28 to impart any desired diameter to device 26 and, more particularly, to tubular structure 28.

Device 26 and, more particularly, tubular structure 28, may be formed of any suitable material known in the art. In particular, tubular structure 28 may be formed of expanded polytetrafluoroethylene (ePTFE) or polyurethane. Tubular structure 28 may be formed of biocompatible materials, such as biocompatible polymers including those which are known. Such polymers may include fillers such as metals, carbon fibers, glass fibers or ceramics. Also, such polymers may include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk may be included in tubular structure 28. In alternative embodiments, tubular structure 28 may be a polymer sleeve.

Tubular structure 28 may be incorporated in a composite structure which also includes a stent structure. The stent structure may include elongate members, such as wires, or a tubular structure having cutouts. Wires may comprise metals, polymers or combinations thereof. The stent structure may be connected to tubular structure 28 by a seal. Tubular structure 28 may be located within the stent structure in coaxial relation therewith. Such a tubular structure 28 which is within the stent structure may be connected thereto such that the tubular structure 28 is in hanging relation to the stent structure. The connection of tubular structure 28 to the stent structure may be provided by one or more threads, filaments or similar connectors.

Desirably, where tubular structure 28 is within a stent structure, tubular structure has a diameter which is substantially the same as the diameter of the stent structure. In such embodiments, the proximal end of the tubular structure 28 is desirably connected to the proximal end of the stent structure and the distal end of the tubular structure 28 is desirably connected to the distal end of the stent structure. Connection of the proximal end of tubular structure 28 and stent structure substantially eliminates any undesirable radial clearance between the proximal ends. Likewise, connection of the distal end of tubular structure 28 and distal end of stent structure substantially eliminates any undesirable radial clearance between the distal ends. Such radial clearance is undesirable because it may provide a path for the digested food fluid to bypass the lumen of tubular structure 28.

The connections of tubular structure 28 to the stent structure within which tubular structure 28 is located limit radially inward displacement thereof. The outer location of the stent structure relative to tubular structure 28 limits radially outward displacement thereof.

In a further alternative embodiment, tubular structure 28 may be located within an outer stent structure, and an inner stent structure may be located within tubular structure 28. Outward radial displacement of tubular structure 28 is limited by the outer stent structure. Inward radial displacement is limited by the inner stent structure. The connection between the tubular structure 28 and one or more stent structures which are within one another in coaxial relation may provide for the adjacent outer and inner surfaces to be contiguous with one another. Alternatively, the connection may provide for a transverse or radial clearance between the tubular structure 28 and one or more stent structures.

Figure 9:
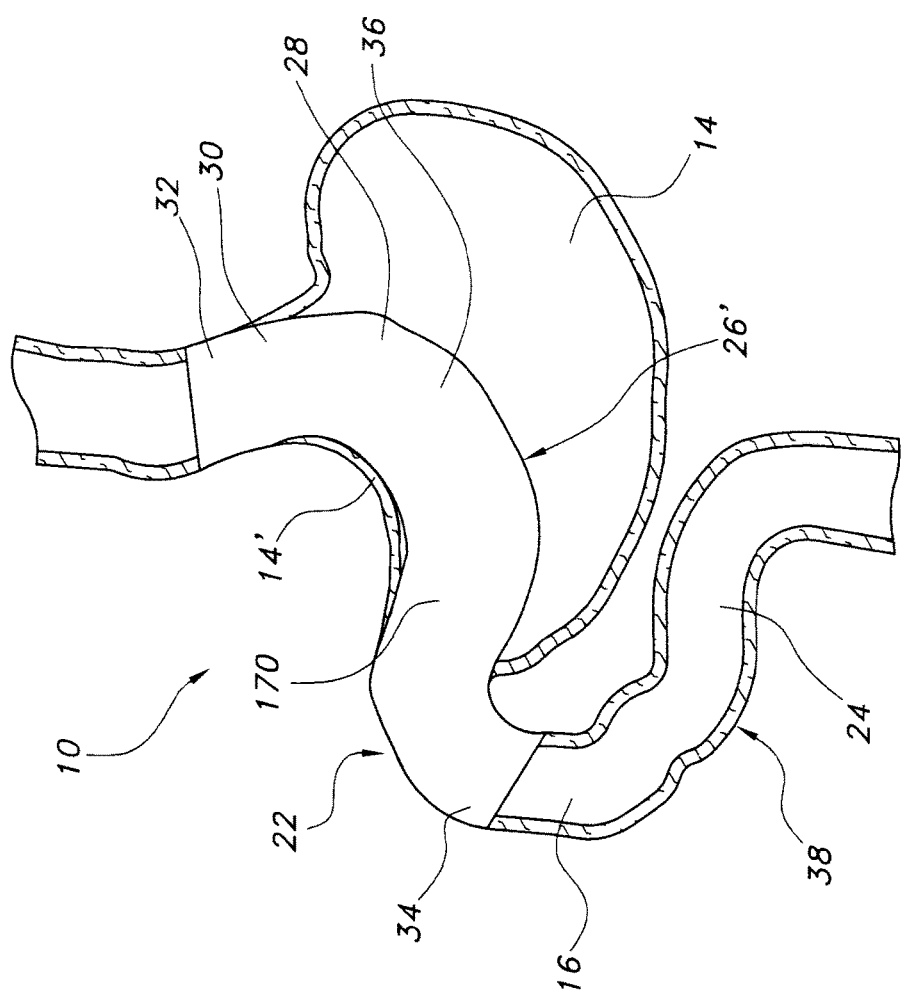
FIG. 9 is an anatomical elevational view of a stomach and adjacent esophagus and small intestine, the wall of the stomach, esophagus, and small intestine being broken away to show an anti-obesity device formed from a bag-like structure in accordance with the present invention.

Tubular structure 28 may be a sleeve structure within which is located a stent structure. It may also comprise a covering or coating which is integral to the wall of the stent device. For example, the sleeve structure 28 may be a PERMALUME® silicone covering for a stent structure constituted by a WALLSTENT® RX Biliary Endoprosthesis, which are made by the Boston Scientific Corporation. In some embodiments, tubular structure 28 may be impermeable or semi-permeable to gastric fluids. In some embodiments, a baggy may be used to promote fullness in the stomach. In particular, in other embodiments, tubular structure 28 may be a bag-like structure or "baggy" 170, as shown in FIG. 9, which bag-like structure or baggy may be used to promote fullness. Where tubular structure 28 is a bag-like structure or "baggy" 170, tubular structure may be made from, but not limited to, for example, neoprene, urethane, silicone, polyethylene terephthalate and combinations thereof. In some embodiments, the covering or coating may be rendered permeable by creating holes or regions of low porosity therethrough.

In some embodiments, device 26 and, more particularly, tubular structure 28 may be a stent structure 140, as shown, for example, in FIGS. 1-2, 4, 5, 6A, 6B, and 7-8. Any suitable stent may be used as device 26 and, more particularly, as tubular structure 28. In particular, various stent types and stent constructions may be employed in the invention. Various stents which are useful include, without limitation, self-expanding stents. The stents may be capable of radially contracting as well and in this sense can best be described as radially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents, including biodegradable and bioabsorbable stents. The configuration of the stent may also be chosen from a host of geometries. For example, wire stents can be fastened into a continuous helical pattern by weaving, twisting, braiding knitting, knotting and the like, with or without a wave-like or zig-zag in the wire, to form a radially deformable stent. Individual rings or circular members can be linked together such as by struts, sutures, welding or interlacing or locking of the rings to form a tubular stent. Tubular stents useful in the invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like. Examples of various stent configurations are shown in U.S. Pat. No. 4,503,569 to Dotter, U.S. Pat. No. 4,856,561 to Hillstead, U.S. Pat. No. 4,580,568 to Gianturco, U.S. Pat. No. 4,732,152 to Wallsten, and U.S. Pat. No. 5,876,448 to Thompson, all of whose contents are incorporated herein by reference. Braided, knitted, and laser-cut stents are particularly useful.

As depicted in FIG. 25, one embodiment of the present invention applies the method of the present invention to a braided stent 140. FIG. 25 is an exploded or enlarged view of the stent 140 to depict the braiding of the stent filaments 142. As used herein the term braiding and its variants refer to the diagonal intersection of elongate filaments 142 so that each filament passes alternately over and under one or more of the other filaments, which is commonly referred to as an intersection repeat pattern. Useful braiding patterns include, but are not limited to, a diamond braid having a 1/1 intersection repeat pattern, a regular braid having a 2/2 intersection repeat pattern or a hercules braid having a 3/3 intersection repeat pattern. The passing of the filaments under and over one and the other results in slidable filament crossings that are not interlooped or otherwise mechanically engaged or constrained.

Figure 31:
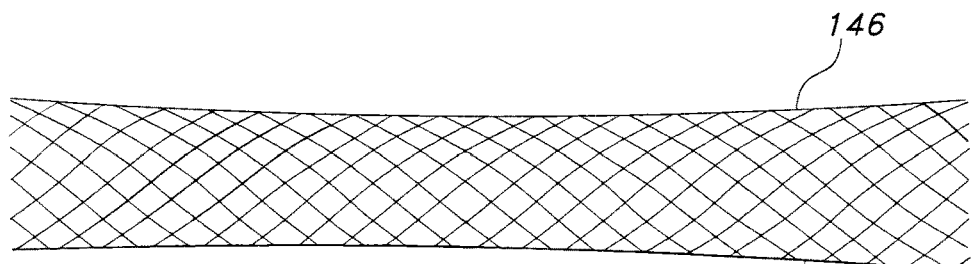
FIG. 31 is a longitudinal view of a wire stent suitable for use in the present invention.

As described above, various stent types and stent constructions may be employed in the invention as the tubular structure 28 and as the mechanical expanding device 46', and the invention can be constructed to accommodate stents of various sizes and configurations. Non-limiting examples of suitable stent geometries for stent 140 are illustrated in FIGS. 31-37. In particular, tubular structure 28 and mechanical expanding device 46' may be a wire stent 144. As shown in FIG. 31, wire stent 144 is a hollow tubular structure formed from wire strand 146 or multiple wire strands. Wire stent 144 may be formed by, for example, braiding or spinning wire strand(s) 146 over a mandrel (not shown). Wire stent 144 is capable of being radially compressed and longitudinally extended for implantation into a bodily lumen. The degree of elongation depends upon the structure and materials of the wire stent 144 and can be quite varied, for example, about 5% to about 200% of the length of wire stent 144. The diameter of wire stent 144 may also become several times smaller as it elongates.

Unitary stent structures may be obtained by braiding and/or filament winding stent wires to obtain complex stent geometries, including complex stent geometries, including complex bifurcated stents. Alternatively, stent components of different sizes and/or geometries may be mechanically secured by welding or suturing. Additional details of wire stents of complex geometry are described in U.S. Pat. Nos. 6,325,822 and 6,585,758, the contents of which are incorporated herein by reference.

Tubular structure 28 and mechanical expanding device 46' may be a stent 140 which has one or more atraumatic open end(s). As used herein, the phrase "atraumatic end," and it variants, refers to a terminal end of a stent which is free of sharp wire ends or other sharp projections or deformities which may cause trauma when implanted into a bodily lumen. In particular, the wires of stent 140 may be braided so as to produce an atraumatic end. For example, certain wires of stent 140 may be extended and looped back to provide an atraumatic end having, for example, no sharp or traumatically pointed bends, no sharp wire ends, and no other traumatically sharp projections or deformities or the like.

Figure 32:
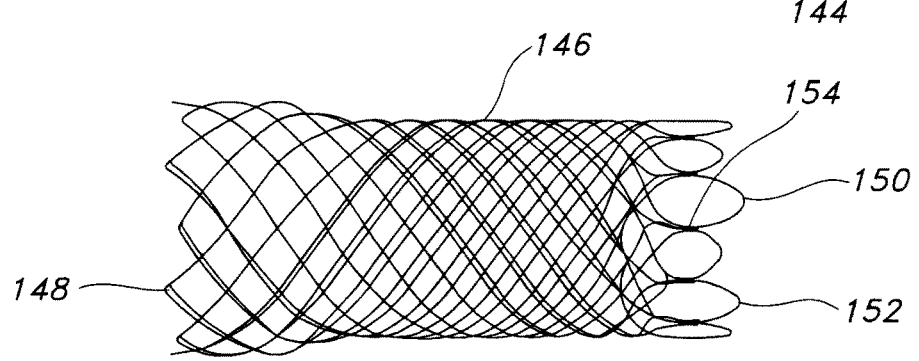
FIG. 32 is a longitudinal view of an atraumatic braided stent for use in the present invention.

In some embodiments, stent 140 may be braided stent 146. As depicted in FIG. 32, braided stent 146 is desirably an atraumatic stent having no sharp terminating members at one or both of the opposed open ends 148, 150. In particular, such a stent desirably has atraumatic ends, i.e., ends which are free or substantially free of loose wire ends or of other sharp projections. The elongate stent wires terminating at open end 150 are mated to form closed loops 152 and adjacently mated wires are secured to one and the other by mechanical means, such as welds 154. The positioning of adjacently mated wires to form closed-loop end designs is further described in U.S. Patent Application Publication Nos. 2005/0049682 A1 and 2006/0116752 A1, the contents of which are incorporated herein by reference. Desirably, the elongate wires terminating at open end 150 are in a cathedral type arch or loop configuration. Further details of the cathedral type of arch or closed-loop configuration may be found in U.S. Patent Application Publication No. 2005/0256563 A1, the contents of which are incorporated herein by reference. The stent wires at the opposed open end 148 may also be free of any sharp terminating points by, for example, commencing braiding of the wires under tension over a pin (not shown) so that the wire ends terminate just at the end 150, where the wire ends may be looped and welded thereat.

Figure 33:
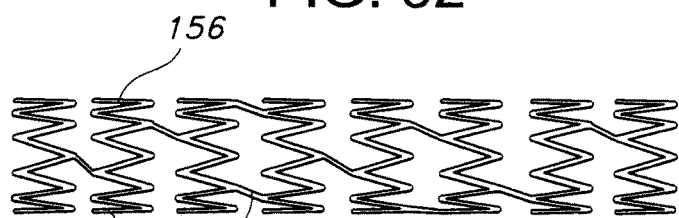
FIG. 33 is a longitudinal view of a zig-zag stent for use in the present invention.
Figure 34:
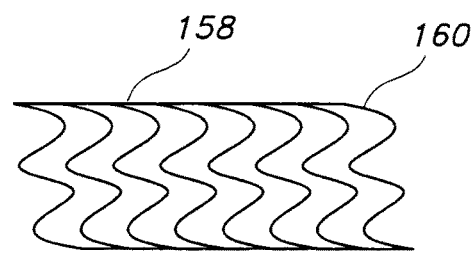
FIG. 34 is a longitudinal view of an alternate zig-zag stent for use in the present invention.

A zig-zag wire stent 156 may also be useful as stent 140. Wire strand 142 may be arranged in what can be described as a multiple of "Z" or "zig-zag" patterns to form a hollow tubular stent. The different zig-zag patterns may optionally be connected by connecting member 146. Further, zig-zag wire stent 156 is not limited to a series of concentric loops as depicted in FIG. 33, but may be suitably formed by helically winding of the "zig-zag" pattern over a mandrel (not shown). For example, as depicted in FIG. 34, zig-zag stent 158 is formed by helically winding at least one stent wire 160 with no interconnections between the helically wound undulating portions. The wire ends (not shown) may be looped and welded to provide no sharp wire ends at the ends of the stent.

Figure 35:
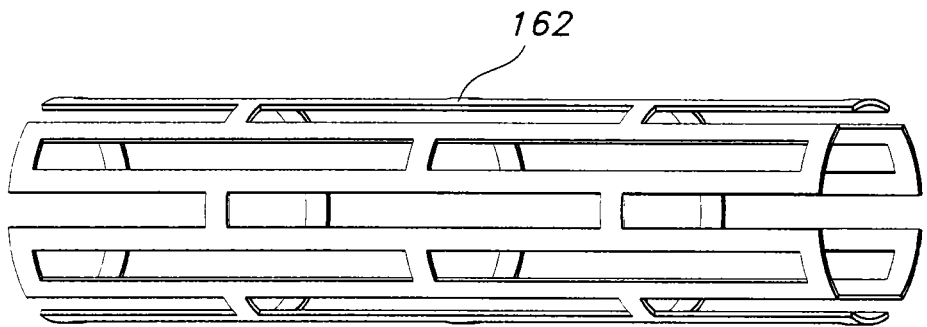
FIG. 35 is a perspective view of a slotted stent for use in the present invention.

A slotted stent 162 may also be useful as stent 140. As depicted in FIG. 35, slotted stent 162 is suitably configured for implantation into a bodily lumen (not shown).

Figure 36:
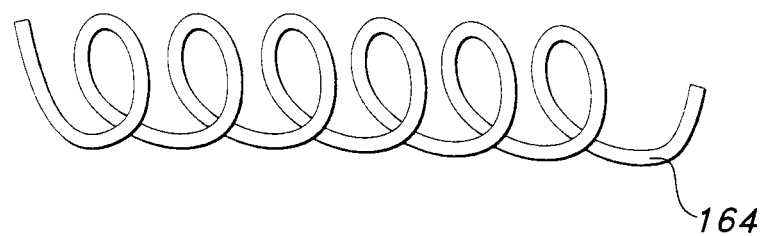
FIG. 36 is a perspective view of a helical coil stent formed of a single wound wire for use in the present invention.
Figure 37:
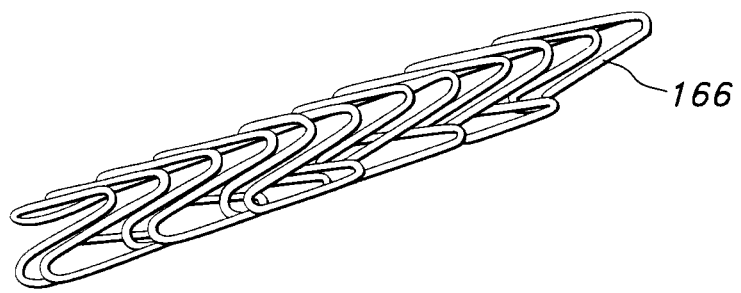
FIG. 37 is a perspective view of a stent having an elongate pre-helically coiled configuration for use in the present invention.

Other useful stents capable of radial expansion are depicted in FIGS. 36 and 37. As depicted in FIG. 36, stent 164 is a helical coil which is capable of achieving a radially expanded state (not shown). Stent 166, as depicted in FIG. 37, has an elongate pre-helically coiled configuration as shown by the waves of non-overlapping undulating windings. These helically coiled or pre-helically stents, commonly referred to as nested stents, are also useful with the practice of one embodiment of the invention. It will be understood that stent 140 may be a stent 164 or stent 166.

Further, as depicted in FIG. 29, the stent 140 may have a straight or substantially straight longitudinal portion 142. The present invention, however, is not so limited. For example, the stent 140 may have a varied diameter, such as a flaring or tapering, along a portion or portion of its longitudinal expanse. One non-limiting example of a varied diameter stent 140 is depicted in FIG. 30. The stent 140 of FIG. 30 may include a longitudinal length 144 and one or two flared ends 147. As depicted in FIG. 30, the flared ends 147 are enlarged flared ends having a diameter greater than the diameter of the longitudinal portion 144 of the stent 140. The stent 140, however, is not so limited, and for example the flared ends 146, individually or in combination, may have a smaller diameter than the diameter of the longitudinal portion 144 of the stent 140. Further, the stent 140 may be repositionable, removable and/or reconstrainable, and/or may include multiple interconnected or non-interconnected stents. For example, the stent 140 may include a loop or element, such as a suture loop or element, a polymeric loop or element, metallic loop or element, and combinations thereof which may be accessible to a user or practitioner, for example by the use of forceps, to reposition, remove and/or reconstrain the stent 140 after it has been delivered, partially or totally, to a bodily lumen. Moreover, a loop or element may be integrally formed as part of the stent 140. Further details of useful repositioning, removing and/or reconstraining loops or elements may be found in U.S. patent application Ser. No. 11/341,540, filed Jan. 27, 2006, and entitled "Stent Retrieval Member And Devices And Methods For Retrieving Or Repositioning A Stent", which published as U.S. Patent Application Publication No. 2006/0190075 A1, and in U.S. patent application Ser. No. 11/432,065, filed May 11, 2006, and entitled "Integrated Stent Repositioning And Retrieval Loop", which published as U.S. Patent Application Publication No. 2006/0276887 A1, the contents of both of which are incorporated herein by reference. Other stent designs may include intermittent stent structures, which may be interconnected by stent wires or other filaments, or may be held in placed apart and flexible orientation by a stent lining or covering.

In some embodiments, stent 140 may be formed of a metal braid formed of a flat wire. In such embodiments, the flat wire may have a width of between 0.001 inches (0.025 mm) and 0.005 inches (0.13 mm) and a thickness of about 0.001 inches (0.025 mm).

The stent 140 may be coated with a polymeric material. For example, the stent wires may be partially or fully covered with a biologically active material which is elutably disposed with the polymeric material. Further, the polymeric coating may extend over or through the interstitial spaces between the stent wires so as to provide a hollow tubular liner or cover over the interior or the exterior surface of the stent, thereby providing a stent-graft device. The polymeric material may be selected from the group consisting of polyester, polypropylene, polyethylene, polyurethane, polynaphthalene, polytetrafluoroethylene, expanded polytetrafluoroethylene, silicone, and combinations thereof. The covering may be in the form of a tubular structure. The silicone covering may be suitably formed by dip coating the stent. Details of such dip coating may be found in U.S. Pat. No. 5,875,448, the content of which is incorporated herein by reference. The present invention is not limited to forming the silicone film by dip coating, and other techniques, such as spraying, may suitably be used. After applying the silicone coating or film to the stent, the silicone may be cured. Desirably, the curing is low temperature curing, for example from about room temperature to about 90° C. for a short period of time, for example from about 10 minutes or more to about 16 hours. The cured silicone covering may also be sterilized by electronic beam radiation, gamma radiation, ethylene oxide treatment and the like. Further details of the curing and/or sterilization techniques may be found in U.S. Pat. No. 6,099,562, the content of which is incorporated herein by reference. Argon plasma treatment of the cured silicone may also be used. Argon plasma treatment of the cured silicone modifies the surface to the cured silicone to, among other things, make the surface less sticky. The invention, however, is not limited to stent-graft devices having polymeric coatings. The graft portion may suitably be formed from polymeric films, polymeric tapes, polymeric tubes, polymeric sheets and textile materials. Textile material may be woven, knitted, braided and/or filament wound to provide a suitable graft. Various biocompatible polymeric materials may be used as textile materials to form the textile structures, including polyethylene terephthalate (PET), naphthalene dicarboxylate derivatives such as polyethylene naphthalate, polybutylene naphthalate, polytrimethylene naphthalate, trimethylenediol naphthalate, ePTFE, natural silk, polyethylene and polypropylene, among others. Moreover, textile materials and stent materials may be co-formed, for example co-braided, to form a stent-graft device. Furthermore, coverings and/or coatings for use with the present invention may have any number of coverings and/or coatings, size, shape, porosity, and/or placement of holes to promote the desired effect of the present invention.

In some embodiments, stent 140 is a joined or welded stent. In such a stent, elongate wires terminating at an open end of the stent are mated, and adjacently mated wires are secured by welds or other suitable means. For example, the wires may be welded together through use of a welding material or the wires may be fused together without the use of a welding material by means of heating and/or melting. Furthermore, the wires may be mechanically joined, such as, for example, through the use of small-sized or microfabricated clamps, crimpable tubes, hypotubes, and the like.

Although the stent 140 may be formed of metals, plastics or other materials, it is preferred that a biocompatible material or construction is used. In particular, the wires or filaments of stents useful in the present invention may be made from a biocompatible material or biocompatible materials. Useful biocompatible materials include, but are not limited to, biocompatible metals, biocompatible alloys, biocompatible polymeric materials, including synthetic biocompatible polymeric materials and bioabsorbable or biodegradable polymeric materials, materials made from or derived from natural sources and combinations thereof. Desirably, the wires are biocompatible metals or alloys made from, for example, nitinol, stainless steel, a cobalt-based alloy such as Elgiloy, platinum, gold, titanium, tantalum, niobium, polymeric materials, and combinations thereof. Useful synthetic biocompatible polymeric materials include, but are not limited to, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, silks, and polytetrafluoroethylenes. The polymeric materials may further include a metallic, glass, ceramic or carbon constituent or fiber. Useful and non-limiting examples of bioabsorbable or biodegradable polymeric materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), polycaprolactone (PCL), polyhydroxybutyrate (PHBT), poly(phosphazene), poly(D,L-lactide-co-caprolactone) (PLA/PCL), poly(glycolide-co-caprolactone) (PGA/PCL), poly(phosphate ester), and the like. Further, stent 140 may include materials made from or derived from natural sources, such as, but not limited to, collagen, elastin, glycosaminoglycan, fibronectin and laminin, keratin, alginate, combinations thereof and the like.

Wires made from polymeric materials also may include radiopaque materials, such as metallic-based powders or ceramic-based powders, particulates or pastes, which may be incorporated into the polymeric material. For example, the radiopaque material may be blended with the polymer composition from which the polymeric wire is formed, and subsequently fashioned into the stent. Alternatively, the radiopaque material may be applied to the surface of the metal or polymer stent. In either embodiment, various radiopaque materials and their salts and derivatives may be used including, without limitation, bismuth, barium and its salts such as barium sulfate, tantalum, tungsten, gold, platinum and titanium, to name a few. Additional useful radiopaque materials may be found in U.S. Pat. No. 6,626,936, which is herein incorporated in its entirety by reference. Metallic complexes useful as radiopaque materials also are contemplated.

Stent 140 may be selectively made radiopaque at desired areas along the wire or may be made fully radiopaque, depending on the desired end-product and application. Furthermore, the wires of stent 140 may have an inner core of tantalum, gold, platinum, or iridium, or a combination thereof, and an outer member or layer of nitinol to provide a composite wire for improved radiopacity or visibility.

Alternatively, the stent 140 may also have improved external imaging under magnetic resonance imaging (MRI) and/or ultrasonic visualization techniques. MRI is produced by complex interactions of magnetic and radio frequency fields. Materials for enhancing MRI visibility include, but are not to be limited to, metal particles of gadolinium, iron, cobalt, nickel, dysprosium, dysprosium oxide, platinum, palladium, cobalt-based alloys, iron-based alloys, stainless steels, or other paramagnetic or ferromagnetic metals, gadolinium salts, gadolinium complexes, gadopentetate dimeglumine, compounds of copper, nickel, manganese, chromium, dysprosium and gadolinium. To enhance the visibility under ultrasonic visualization the stent 140 of the present invention may include ultrasound resonant material, such as but not limited to gold. Other features, which may be included with the stent 140 of the present invention, include radiopaque markers; surface modification for ultrasound, cell growth or therapeutic agent delivery; varying stiffness of the stent or stent components; varying geometry, such as tapering, flaring, bifurcation and the like; varying material; varying geometry of stent components, for example tapered stent filaments; and the like.

Desirably, the wires are made from nitinol, or a composite wire having a central core of platinum and an outer layer of nitinol. Desirably, the inner core of platinum represents about at least 10% of the wire based on the overall cross-sectional percentage. Moreover, the nitinol desirably has not been treated for shape memory such as by heating, shaping and cooling the nitinol at its martensitic and austenitic phases. Further details of suitable composite wires may be found in U.S. Patent Application Publication 2002/0035396 A1, the contents of which are incorporated herein by reference.

The wires of stent 140 may have any suitable diameter. Desirably, the wires are relatively thin and have a diameter of about 0.01 to 0.02 inches.

Moreover, stent 140 may contain any suitable number of wires. Desirably, an even number of wires is used. For example, in some embodiments, stent 140 may contain from about 10 to about 36 wires. Furthermore, stent 140 also may include apertures and/or discontinuities (not shown) along portions of the stent wall.

The stent 140 may have coverings, films, coatings, and the like disposed over, under or throughout or embedding stent 140. Any suitable covering, film, coating, and the like may be used in combination with stent 140. In particular, stent 140 may be fully, substantially or partially covered with such a covering, film, coating, and the like on an external and/or internal surface of stent 140. The covering may be, for example, a graft covering in the form of a hollow, tubular graft structure.

For example, as depicted in FIG. 26, the stent 140 may include a covering 149, desirably a polymeric covering, disposed over the longitudinal length or a portion of the longitudinal length of the stent 140. Further, as depicted in FIG. 27, the stent 140 may include a liner 151, desirably a polymeric liner, disposed within the longitudinal length or a portion of the longitudinal length of the stent 140. Moreover, as depicted in FIG. 28, the stent 140 may include both a covering 149 and a liner 151, desirably a polymeric covering and liner which include the same or different polymeric materials, disposed over and within the longitudinal length or a portion of the longitudinal length of the stent 140. The covering and the liner of FIG. 28 may be a unitary film or coating that embeds or partially embeds the stent 140. The covering 149 and/or the liner 151 may be in the form of a tubular structure, for example composed of polymeric material and/or silicone. The covering 149 and/or the liner 151 may also comprise any plastic or polymeric material, desirably a somewhat hard but flexible plastic or polymeric material. The covering 149 and/or the liner 151 may be transparent or translucent, desirably substantially or partially transparent.

The coverings and/or the liner of the present invention may be made from a "textile" material, from a "non-textile" material, or from a combination thereof. As used herein, the term "textile" refers to a material, such as a yarn, that may be knitted, woven, braided, or the like, into a structure, such as a hollow, tubular structure. As used herein, the term "non-textile" refers to a material formed by casting, molding, spinning or extruding techniques to the exclusion of typical textile forming techniques, such as braiding, weaving, knitting, and the like. In particular, the covering 149 and/or the liner 151 may be constructed of any suitable biocompatible materials, such as, but not limited to, polymers and polymeric materials, including fillers such as metals, carbon fibers, glass fibers or ceramics.

Useful covering 149 and/or liner 151 materials include, but are not limited, polyethylene, polypropylene, polyvinyl chloride, polytetrafluoroethylene (PTFE), including expanded polytetrafluoroethylene (ePTFE), fluorinated ethylene propylene, fluorinated ethylene propylene, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polyimides, polycarbonates, polyaldehydes, polyether ether ketone, natural rubbers, polyester copolymers, styrene-butadiene copolymers, polyethers, such as fully or partially halogenated polyethers, silicones, and copolymers and combinations thereof.

The coating or coatings may be on the stent 140, components of the stent 140, and combinations thereof. The stent components, in part or in total, may be temporary, for example bioabsorbable, biodegradable, and the like, or may be permanent (i.e., not substantially bioabsorbable or biodegradable), for example the above-described biocompatible metals, alloys and polymers.

Desirably, the stent 140 includes braided polyester filaments, such as PET polyester filaments. Further, in some applications, the stent 140 is desirably embedded in a coating of silicone. Additional details of such desirable stents are described in U.S. Pat. No. 6,162,244, the contents of which are incorporated herein by reference.

When a silicone covering is used, the silicone may be disposed on external surfaces of the stent 140 and/or on internal surfaces of the stent 140. Such a silicone covering may be in the form of a coating or film and may be suitably formed by dip-coating the stent. Details of such dip-coating may be found in U.S. Pat. No. 5,875,448, the contents of which are incorporated herein by reference. Moreover, other techniques, such as spraying, may suitably be used to form the silicone covering. After applying the silicone coating or film to the stent, the silicone may be cured. Desirably, the curing is low temperature curing. For example, the curing desirably occurs from about room temperature to about 90° C. for a short period of time which may be, for example, from about 10 minutes or more to about 16 hours. The cured silicone covering also may be sterilized by electronic beam radiation, gamma radiation ethylene oxide treatment, and the like. Further details of the curing and/or sterilization techniques may be found in U.S. Pat. No. 6,099,562, the contents of which are incorporated herein by reference. Argon plasma treatment of the cured silicone also may be used. Argon plasma treatment of the cured silicone modifies the surface of the cured silicone to, among other things, make the surface less sticky.

Suitable textile materials for use in the present invention may be formed from synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament or spun-types. As is well-known, the type and denier of the yarn chosen may be selected in a manner which forms a prosthesis and, more particularly, a vascular structure having desirable properties.

The yarns for use in textile graft coverings of the present invention may be knitted, woven, or braided in any manner known in the art. The knit may be a circular knit or may be a flat knitted tubular knit. Useful knits include, but are not limited to, a high stretch knit, a locknit knit (which also is referred to as tricot or jersey knit), reverse locknit knits, sharkskin knits, queenscord knits, and velour knits. Useful high stretch, warp-knitted patterns include those with multiple patterns of diagonally shifting yarns, such as certain modified atlas knits which are described in U.S. Pat. No. 6,540,773, the contents of which are incorporated herein by reference. Other useful high-stretch, warp knitted patterns include certain patterns with multiple needle underlap and one needle overlap, such as those patterns described in U.S. Pat. No. 6,554,855 and U.S. Patent Application Publication No. 2003/0204241 A1, the contents of which are incorporated herein by reference. U.S. Pat. No. 5,653,746, the contents of which are incorporated herein by reference, further describes useful knits. Useful braids include, but are not limited to, those described in U.S. Pat. No. 5,653,746, the contents of which are incorporated herein by reference. Useful weaves include, but are not limited to, a plain or regular weave, a basket weave, a twill weave, a satin weave, a velour weave, a circular weave, a flat tubular weave, or the like. Suitable textiles and methods for making the same are further discussed in U.S. application Ser. No. 11/025,571, filed Dec. 29, 2004, the contents of which are incorporated herein by reference.

In some embodiments, tubular structure 28 and, more particularly, stent 140 may be treated with any suitable therapeutic agent. Non-limiting examples of suitable therapeutic agents include the following: anti-thrombogenic agents (such as heparin, heparin derivatives, urokinase, and PPack (dextrophenylalanine proline arginine chloromethylketone)); anti-proliferative agents (such as enoxaprin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms. Agents for reducing hunger, improving digestion, moving food along the gastrointestinal tract, neutralizing digestion, hormones and the like are also useful with the practice of the present invention.

Suitable stents, materials for stents and delivery devices for use in the present invention include those discussed in U.S. Pat. Nos. 7,172,617; 7,311,031; 7,419,502; 7,419,503; and 7,462,192; and U.S. Patent Application Publication Nos. 2005/0049682; 2005/0256563; 2006/0100688; 2006/0190075; 2006/0276887; 2007/0106370; 2007/0118206; 2007/0123969; 2007/0270931; 2007/0270937; 2007/0273932; 2008/0009934; 2008/0262592; 2008/0288054; 2008/0312734; 2009/0048653; 2009/0054972; 2009/0082840; 2009/0171434; 2009/0182407; and 2009/0192518; the contents of all of which are incorporated herein by reference.

In some embodiments, stent structure 140 may be a WALLSTENT® RX Biliary Endoprothesis made by the Boston Scientific Corporation. Alternatively, the stent structure 140 may be a NIR® Biliary Stent System made by the Boston Scientific Corporation. Further alternative stent structures are possible, including, but not limited to Wall-Flex® Stent devices.

Coating layer 42 may be formed of any suitable material known in the art. Suitable materials for coating layer 42 include, for example, any of the coating materials described herein. Desirably, coating layer is a membrane which is impermeable or semi-permeable to gastric fluids. Coating layer 42 may be formed directly on stent 140 of the present invention or on a graft layer and/or liner covering stent 140. The coating may be on the inside of the stent to promote food movement therethrough.

In some embodiments, a device 52 for inducing weight loss in a patient according to the present invention is an inflatable structure which includes (a) at least one first panel 54 including a proximal end 56 and a distal end 58; (b) at least one second panel 60 including a proximal end 62 and a distal end 64; and (c) a channel 66 therebetween, as shown in FIG. 10, which is a perspective view of device 52 prior to inflation. As shown in FIG. 10, proximal end 56 of first panel 54 is desirably aligned with proximal end 62 of second panel 60. As further shown in FIG. 10, distal end 58 of first panel 54 is desirably aligned with distal end 64 of at least one second panel 60. As further shown in FIG. 10, device 52 includes attachment seams 72 which secure the first panel 54 and the second panel 60 together along the longitudinal length L of device 52 and which also function to form channel 66 between first panel 54 and second panel 60. As shown in FIG. 10, device 52 has a proximal portion 74, a central portion 78, and a distal portion 76.

As shown in FIG. 11, which is a front view of the device 52 which is shown in FIG. 10, first panel 54 includes central portions 68', 68", proximal portions 56', 56", and distal portions 58', 58". As shown in FIG. 12, which is a back view of the device 52 which is shown in FIG. 11, second panel 60 includes central portions 70', 70", proximal portions 62', 62", and distal portions 64', 64".

Each of central portions 68', 68" of first panel 54 is desirably shaped as shown in FIG. 11 and has a diameter which is greater than the diameter of each of proximal portions 56', 56" and distal portions 58, 58". Moreover, each of central portions 70', 70" of second panel 60 is desirably shaped as shown in FIG. 12 and has a diameter which is greater than the diameter of each of proximal portions 62', 62" and distal portions 64', 64".

With further reference to FIGS. 11 and 12, it will be appreciated that the dimensions of central portions 70', 70" are the same or substantially the same as the dimensions of central portions 68', 68". Moreover, it will be appreciated that the dimensions of proximal portions 56', 56" are desirably the same or substantially the same as the dimensions of proximal portions 62', 62". It also will be appreciated that the dimensions of distal portions 58', 58" are desirably the same or substantially the same as the dimensions of distal portions 64', 64".

Figure 13:
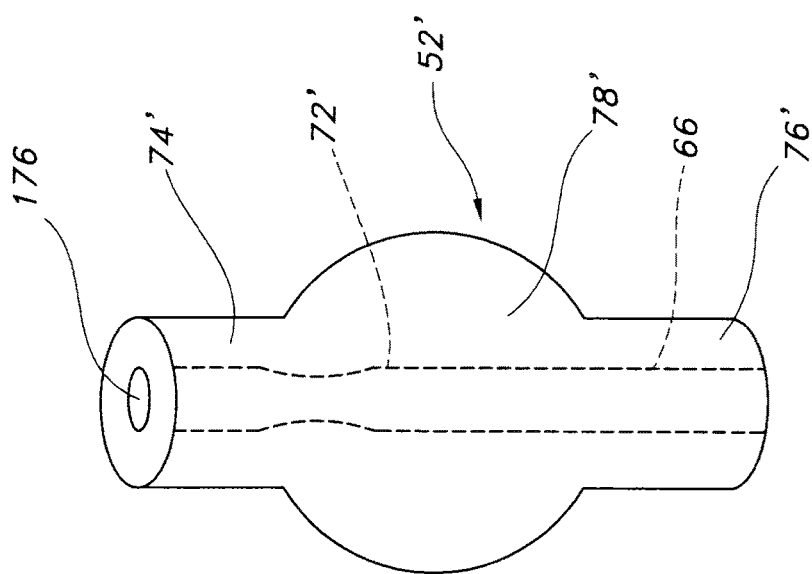
FIG. 13 is a perspective view of the anti-obesity device shown in FIGS. 10-12 after inflation.

In some embodiments, device 52 may be inflated to form an inflated device 52', as shown in FIG. 13, which is suitable for insertion into a stomach 14. Upon inflation, channel 66 has an internal lumen 176 which acts as a conduit through which ingested food 80 may flow from esophagus 12 to stomach 14. Moreover, upon inflation, proximal portion 74 inflates to form a circumferential portion 74' which is sized to fit within the distal segment 44 of esophagus 12. Likewise, distal portion 76 inflates to form a circumferential portion 76' which is sized to fit within proximal end 22 of small intestine 38 and, more particularly, within proximal end 22 of duodenum 16. Additionally, upon inflation, central portion 78 inflates to from a circumferential portion 78' which has a diameter which is less than the diameter of the stomach 14 into which device 52 is placed. The inflated portion may take any geometry desirable to anchor the stent and/or to promote a feeling of fullness, i.e., satiety, with the stomach.

Figure 14:
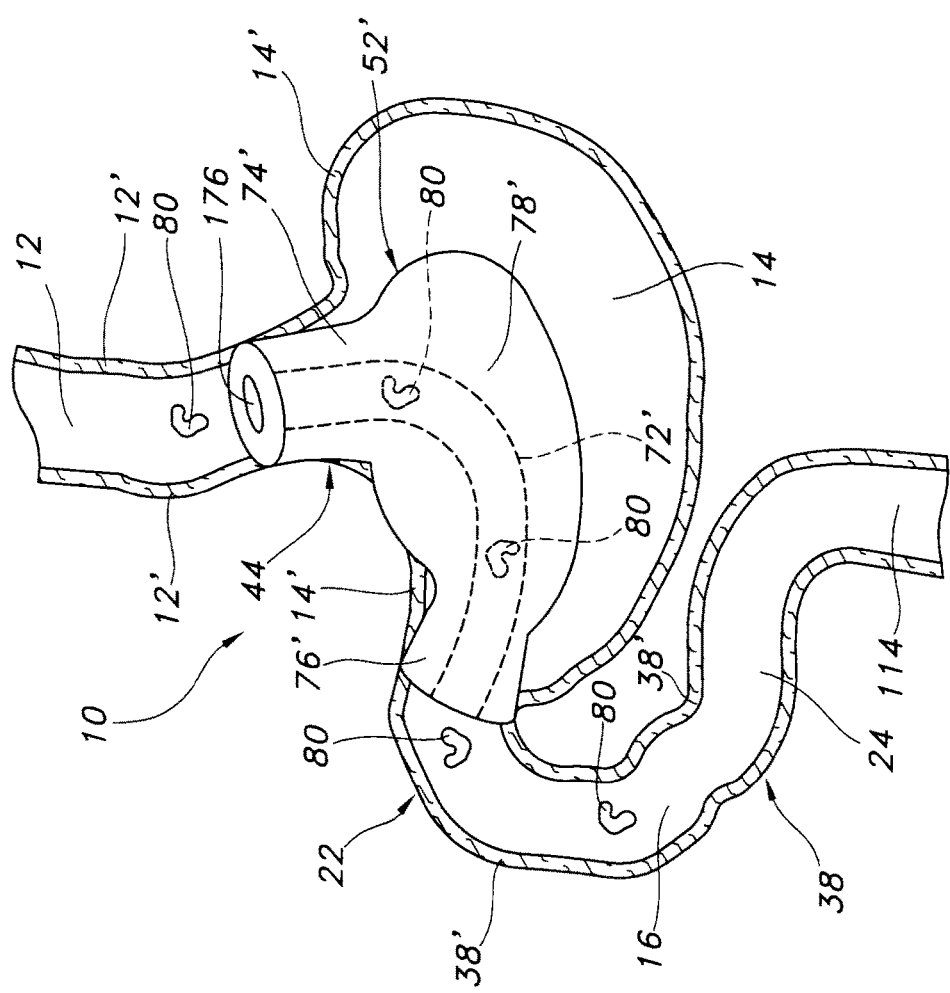
FIG. 14 is an anatomical elevational view of a stomach and adjacent esophagus and small intestine, the wall of the stomach, esophagus, and small intestine being broken away to show an exploded view of anti-obesity device as shown in FIG. 13 positioned in the gastrointestinal system in accordance with the present invention.

In some embodiments, a method for inducing weight loss includes the step of inserting device 52 into the gastrointestinal system of a patient. In particular, in some embodiments, such a method includes the step of inserting uninflated device 52 into the gastrointestinal system of a patient. In such embodiments, uninflated device 52 is positioned such that proximal portion 74 is positioned within the distal segment 44 of esophagus 12, such that central portion 78 is positioned within stomach 14, and such that distal portion 76 is positioned within duodenum 16 of small intestine 38. Upon inflation, proximal portion 74' of device 52' becomes secured within the distal segment 44 of esophagus 12, while distal portion 76' of device 52' becomes secured within the duodenum 16 of small intestine 38, as shown in FIG. 14, which is an exploded view of device 52' as shown in the FIG. 13 after it is positioned in the gastrointestinal system and, more particularly, alimentary canal 10, in accordance with the present invention. As is apparent from FIG. 14, device 52' is flexible enough to conform to the particular contours of gastrointestinal system and, more particularly, alimentary canal 10. Channel 66 (shown in hatch marks) in FIGS. 13 and 14 is a conduit for ingested food 80 (shown in hatch marks when within channel 66) passing from esophagus 12 to small intestine 38.

As will be appreciated from FIG. 14, inflated device 52', when placed in gastrointestinal system and, more particularly, alimentary canal 10, works to induce weight loss by restricting portions of the digestive system. In particular, inflated device 52', when placed in gastrointestinal system and, more particularly, alimentary canal 10, closes off portions of stomach 14 and reduces the volume of food which passes through stomach 14 due to channel 66. As a result, an individual who has such a device in his or her stomach will feel satiated upon eating a smaller portion size and has an increased likelihood of losing weight as a result of reduced calorie intake. Moreover, in some embodiments, inflatable device 52' is impermeable or semi-permeable to gastric fluids. As a result, inflated device 52' eliminates digestion in stomach 14 by preventing the mixing of ingested food 80 with gastric fluids or reduces digestion in stomach 14 by reducing the mixing of ingested food 80 with gastric fluids, thereby reducing or eliminating digestion in the stomach and consequently inducing weight loss.

Inflated device 52' may have any overall length desired. Moreover, inflated proximal end 74' of inflated device 52' and inflated distal end 76' may have any length desired. Although not shown, it will be understood that, in some embodiments, distal end 76' is long enough such that ingested food 80 passing through channel 66 exits into the small intestine at the jejunum 114 (which is the section of small intestine 38 adjacent to duodenum 16) and not the duodenum 16. As a result, the amount of digestion and the amount of reabsorption of the byproducts of digestion in the duodenum 16 is decreased, thereby inducing weight loss.

In some embodiments, there is provided a method for making a device for inducing weight loss in a patient. The method involves the steps of providing at least two panels 54, 60 and attaching said panels in abutting relationship.

Panels 54, 60 are then joined along length 1 by means of seams 72 to form a channel 66 therebetween as shown in FIGS. 10 to 12.

Panels 54, 60 may be made of any suitable material. In particular, panels 54, 60 are made from any flexible materials which are capable of being inflated. For example, panels 54, 60 may be made from urethane sheets or a coated mesh/fabric. In some embodiments, at least one of panels 54, 60 may be made of a material which is impermeable or semi-permeable to gastric fluids. Desirably, in some embodiments, both of panels 54, 60 are made of a material which is impermeable or semi-permeable to gastric fluids. Inflation fluids may include gases, liquids, gels, foams, and the like, or combinations thereof.

Panels 54, 60 may be attached by any suitable means known in the art. In particular, panels 54, 60 may be joined together by means of any adhesive known in the art or by means of welding such as radio-frequency or ultrasonic welding.

In some embodiments, independent chambers may be created to allow the external and internal diameters to be tailored by selective inflation of the chambers. For example, a single inflatable chamber may have only a single fill pressure as a tuning parameter. While such a single fill pressure may be varied, multiple fill chambers would allow additional tuning opportunities as pressures within the different independent chambers could be individually adjusted. In such a case the multiple independent chambers may not be in fluid communication with each other or may have pressure control (not shown) among the individual chambers. For example, it may be useful to provide an independent chamber at a region which traverses the pylorus so that the compliance in this region may be tuned separately from the rest of the device of the present invention.

In some embodiments, devices in accordance with the present invention may be made using more than two sheets of a flexible material to create desired three dimensional shapes which can be used to induce weight loss when placed in the gastrointestinal system of a patient. In other words, any suitable number of sheets of flexible material may be used for the device of the present invention.

Figure 15:
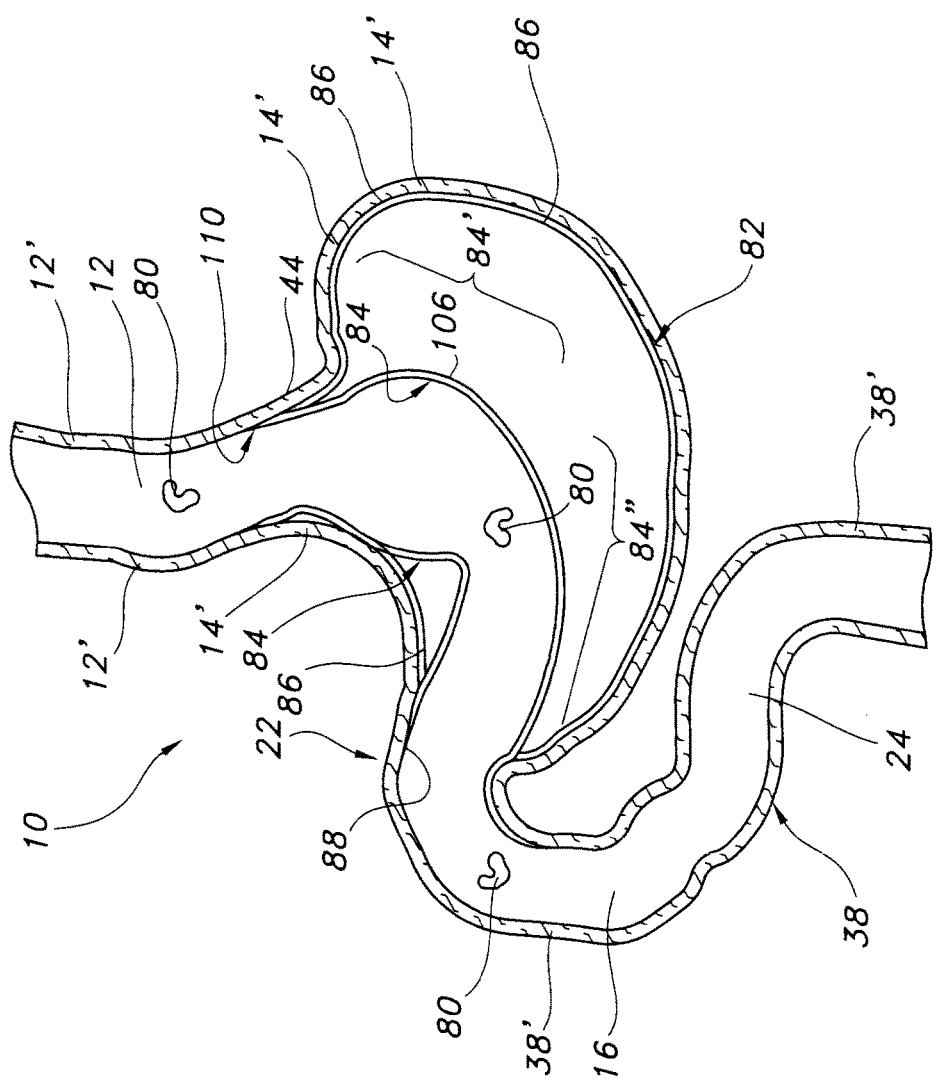
FIG. 15 is an anatomical elevational view of a stomach and adjacent esophagus and small intestine, the wall of the stomach, esophagus, and small intestine being broken away to show an exploded view of an anti-obesity device including an inner structure and an outer structure positioned in the gastrointestinal system in accordance with the present invention.

In some embodiments, a device 82 for inducing weight loss in a patient according to the present invention includes at least one inner structure 84 and at least one outer structure 86. Desirably, inner structure 84 includes an impermeable or semi-permeable membrane. In particular, in some embodiments, inner structure 84 is made from a membrane which is impermeable or semi-permeable to gastric fluids. In other embodiments, inner structure 84 is coated with a membrane 106 which is impermeable or semi-permeable to gastric secretions as shown in FIG. 15. Desirably, outer structure 86 is made from a material which is permeable to gastric fluids. Moreover, outer structure 86 desirably does not include a coating.

In some embodiments, a method for inducing weight loss includes the step of inserting device 82 into the gastrointestinal system 10 of a patient. In such embodiments, method involves positioning device 82 within the gastrointestinal system and, more particularly, alimentary canal 10 such that proximal end 110 of device 82 is positioned within the distal segment 44 of esophagus 12 and such that distal portion 88 of device 82 is positioned within proximal end 22 of duodenum 16 of small intestine 38. In such embodiments, proximal end 110 of device 82 is desirably sized to fit within distal segment 44 of esophagus 12, and distal end 88 of device 82 is desirably sized to fit within proximal end 22 of duodenum 16 of small intestine 38.

Inner structure 84 functions to guide ingested food 80 flowing from esophagus 12 through stomach 14 and into duodenum 16 of small intestine 38 as shown in FIG. 15. Outer structure 86 leans against the inner wall 14' of stomach 14 as shown in FIG. 15 and stabilizes inner structure 84.

Inner structure 84 and outer structure 86 of device 82 may have any suitable shape. In particular, outer structure 86 is desirably capable of conforming to the inner wall 14' of stomach 14. Although inner structure 84 is shown in FIG. 15 as having at least two portions 84', 84" of different dimensions, it will be appreciated that inner structure 84 may have any suitable shape and, in some embodiments, may be a tubular structure having a shape which is analogous to the shape of inner structure 92 shown in FIG. 16.

Inner structure 84 and outer structure 86 may be formed from any suitable material known in the art. Suitable materials for inner structure 84 and for outer structure 86 include any of the suitable materials described herein.

As will be appreciated from FIG. 15, device 82, when placed in gastrointestinal system 14, works to induce weight loss by restricting portions of the digestive system and by diverting gastric fluids into the small intestine 38. In particular, device 82, when placed in gastrointestinal system and, more particularly, alimentary canal 10, closes off portions of stomach 14 and reduces the volume of ingested food 80 which passes through stomach 14 due to inner structure 84. As a result, an individual who has such a device 82 in his or her stomach will feel satiated upon eating a smaller portion size and has a greater likelihood of losing weight as a result of reduced calorie intake. Moreover, in some embodiments, inner structure 84 is impermeable or semi-permeable to gastric fluids. As a result, inner structure 84 eliminates digestion in the stomach by preventing the mixing of ingested food with gastric fluids or reduces digestion in the stomach by reducing the mixing of ingested food with gastric fluids, thereby inducing weight loss.

In embodiments where outer structure 86 is permeable to gastric fluids, gastric fluids are allowed to pass into the small intestine 38. As a result, some digestion of ingested food occurs in small intestine 38. However, the amount of digestion which occurs in the small intestine 38 is less than the amount of digestion which would have occurred in the stomach 14 in the absence of device 82 and, more particularly, in the absence of inner structure 84. As a result, the amount of digestion is further reduced, thereby further inducing weight loss. Moreover, digestion is a multi-component process that begins at the mouth and ends at the anus. Some key elements in weight loss are satiety and absorption of calories from ingested foods or nutrients. The present invention addresses both of these elements by improving the sense of satiety because the stomach is constantly filled with the device 26 and by passing food into the small intestine where the food is broken down less by the stomach because of limited contact with the stomach walls and gastric juices and less interaction with the mechanical action of the stomach.

Device 82 may have any length desired and any shape desired. In particular, proximal end 110 of device 82 and distal end 88 of device 82 may have any length desired. In some embodiments, length of distal end 88 may be long enough such that ingested food 80 passes into the small intestine at the jejunum 114 and not the duodenum 16. As a result, the amount of digestion and the amount of reabsorption of the byproducts of digestion in the duodenum 16 is decreased, thereby inducing weight loss. The device may have an outer structure in the shape of a bellows or a loose covering to simply fill spaces, for example, instead of inflating, it fills the stomach with device material, such as fabric.

Figure 16:
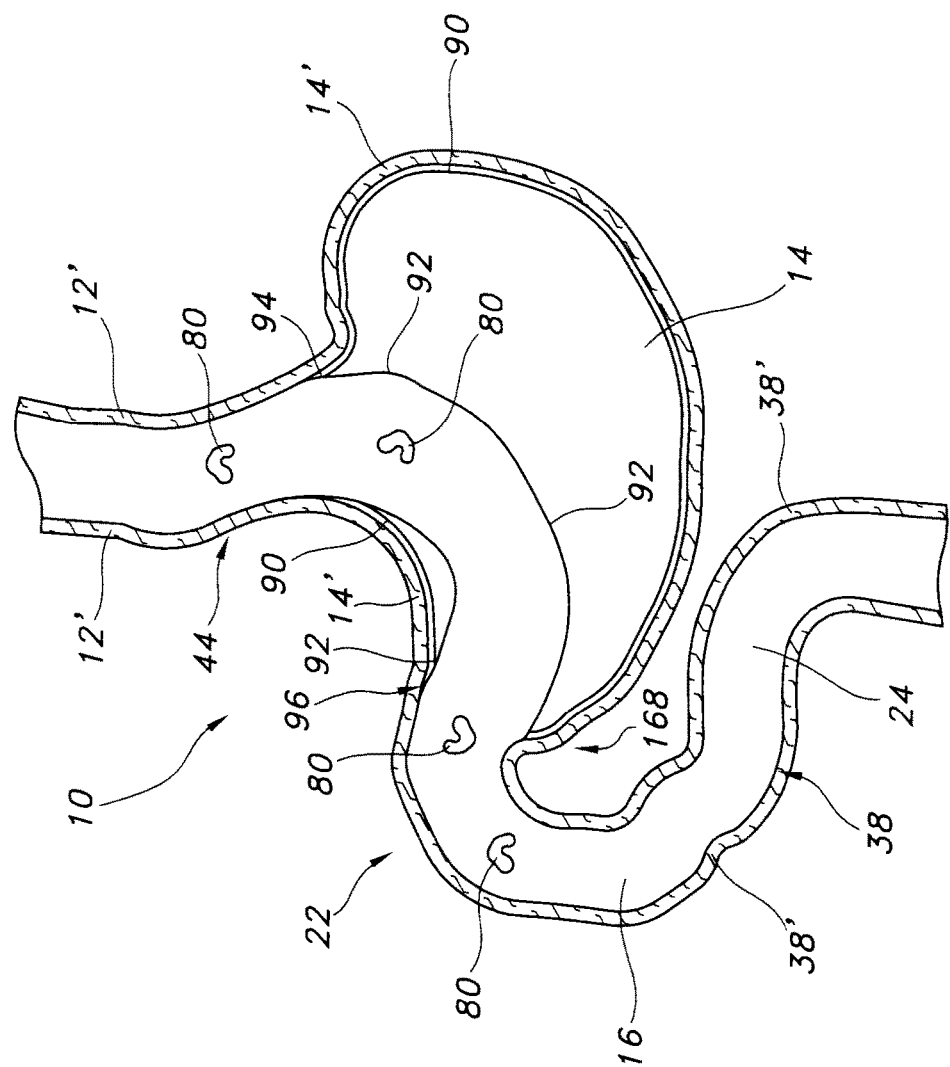
FIG. 16 is an anatomical elevational view of a stomach and adjacent esophagus and small intestine, the wall of the stomach, esophagus, and small intestine being broken away to show an exploded view of two structures positioned in the gastrointestinal system in accordance with a method of the present invention.

In some embodiments, a method for inducing weight loss includes the step of inserting a outer structure 90 and a separate inner structure 92 into the gastrointestinal system and, more particularly, alimentary canal 10 of a patient as shown in FIG. 16. In some embodiments, outer structure 90 is first positioned in stomach 14 and thereafter inner structure 92 is positioned within outer structure 90. In other embodiments, inner structure 92 is first inserted into stomach 14 and outer structure 90 is positioned around inner structure 92. Desirably, proximal end 94 of outer structure 90 is sized to fit within distal segment 44 of esophagus 12 and distal end 96 of outer structure 90 is sized to fit within duodenum 16 of small intestine 38.

Desirably, outer structure 90 is a stabilizing structure and is desirably shaped and positioned within stomach 14 such that it leans against the inner wall 14' of stomach 14 as shown in FIG. 16. Inner structure 92 is sized to fit within outer structure 90. Although inner structure 92 is shown as a tubular structure in FIG. 16, inner structure 92 may have any shape including a shape which is analogous to the shape of inner structure 84 shown in FIG. 15.

Inner structure 92 functions to guide ingested food 80 flowing from esophagus 12 through stomach 14 into duodenum 16 of small intestine 38 as shown in FIG. 16. Outer structure 90 leans against the inner wall 14' of stomach 14 as shown in FIG. 14 and stabilizes inner structure 92.

Inner structure 92 and outer structure 90 may be formed from any suitable material known in the art. Suitable materials for inner structure 92 and for outer structure 90 include any of suitable materials described herein.

As will be appreciated from FIG. 16, outer structure 90 and inner structure 92, when placed in gastrointestinal system and, more particularly, alimentary canal 10, work cooperatively to induce weight loss by restricting portions of the digestive system and by diverting gastric fluids into the small intestine 38. In particular, outer structure 90 and inner structure 92, when placed in gastrointestinal system and, more particularly, alimentary canal 10, work cooperatively to close off portions of stomach 14 and reduce the volume of ingested food 80 which passes through stomach 14. As a result, an individual who has outer structure 90 and inner structure 92 in his or her stomach will feel satiated upon eating a smaller portion size and will have an increased likelihood of losing weight as a result of reduced calorie intake.

Moreover, in some embodiments, inner structure 92 is impermeable or semi-permeable to gastric fluids. As a result, inner structure 92 eliminates and/or reduces digestion in stomach 14 by preventing the mixing of ingested food with gastric fluids or reduces digestion in the stomach 14 by reducing the mixing of ingested food with gastric fluids, thereby inducing weight loss.

In embodiments where outer structure 90 is permeable to gastric fluids, gastric fluids are allowed to pass into the small intestine 38. As a result, some digestion of ingested food occurs in small intestine 38. However, the amount of digestion which occurs in the small intestine 38 is less than the amount of digestion which would have occurred in the stomach 14 in the absence of outer structure 90. As a result, the amount of digestion is further reduced, thereby further inducing weight loss. Moreover, digestion of different materials may also depend on the location of those material within the body. For example, starch, sugars and proteins are typically digested in the stomach while fats are typically digested in the intestine.

Figure 17:
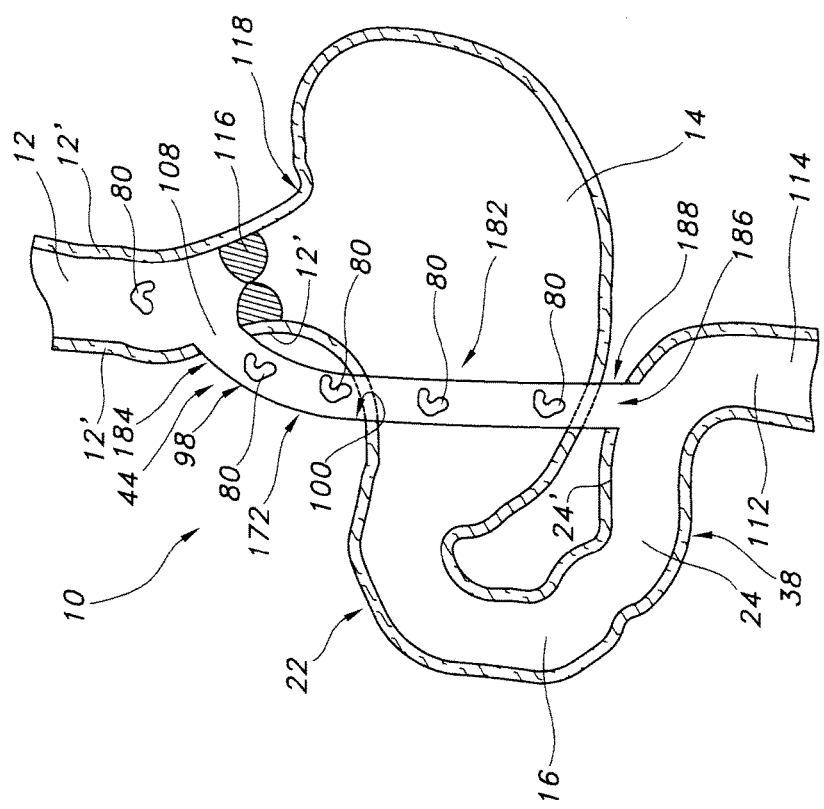
FIG. 17 is an anatomical elevational view of a stomach and adjacent esophagus and small intestine, the wall of the stomach, esophagus, and small intestine being broken away to show a restrictive device positioned in the gastrointestinal system in accordance with an esophageal diversion method of the present invention.

In some embodiments, there is provided a method for inducing weight loss in patient which involves an esophageal diversion. The method involves inserting a diverter structure 172 having an outer surface 98 and an inner surface 100, a proximal end 102 and a distal end 104, and a central portion 182 within a gastrointestinal system and, more particularly, an alimentary canal 10 as shown in FIG. 17. In particular, distal portion 44 of esophagus 12 is laparoscopically or transluminally cut to form an opening 108 in the wall 12' of the esophagus 12 and proximal end 184 of diverter structure 172 is positioned within opening 108 as shown in FIG. 17. Distal end 24 of duodenum 16 is then laparoscopically or transluminally cut to form an opening 186 in the wall 24' of the distal end 24 of duodenum 16. Distal end 188 of diverter structure 172 is then positioned within opening 186. As shown in FIG. 17, central portion 182 of diverter structure 172 transverses stomach 14 from the esophagus 12 to distal end 24 of duodenum 16 of small intestine 38 external to the stomach 14. Although not shown, it will be understood that, in some embodiments, distal end 188 of diverter structure 172 may be positioned such that it is positioned within an opening which is laparoscopically or transluminally cut in proximal end 112 of jejunum 114. Structure 172 may be secured in place with any of the above mentions constructions or methods, including stent flares, sutures, adhesives, and the like or combinations thereof.

In such embodiments, a restrictive device 116 is desirably placed within the distal segment 44 of esophagus 12 between the opening 108 where diverter structure 172 is attached to esophagus 12 and the point 118 where the esophagus joins to the stomach 14. Restrictive device 116 prevents ingested food 80 from passing into stomach 14 from esophagus 12 as shown in FIG. 17. As a result, ingested food 80 is diverted from esophagus 12 into tubular structure 96 and then into small intestine 38.

Restrictive device 116 may completely or partially block off stomach 14 from the esophagus 12. Because stomach 14 is completely or partially bypassed, digestion in the stomach 14 does not occur or occurs to a lesser extent, thereby inducing weight loss. Moreover, in embodiments where distal end 104 of structure 172 is positioned within an opening in jejunum 114 or the distal end 24 of duodenum 16, digestion and reabsorption of the byproducts of digestion in the upper portion of duodenum 16 may be bypassed, which also induces weight loss.

Restrictive device 116 may be any suitable device known in the art. Desirably, restrictive device 116 is a Y-adapter as shown in FIG. 17.

Diverter structure 172 may be any suitable structure known in the art. In some embodiments, diverter structure 172 is a tubular structure such as shown in FIG. 17. Suitable materials from which diverter structure 172 is made include any of the above described material of construction. Diverter structure 172 may also have any and all of the above mentioned constructions.

The devices of the present invention may be delivered to a bodily lumen and, more particularly, the alimentary canal 10 using any suitable delivery device known in the art. In some embodiments, a wire is used to deliver an anti-obesity device of the present invention to a bodily lumen. In other embodiments, a rapid exchange catheter such as the rapid exchange catheter disclosed in U.S. Pat. No. 6,592,549, the full contents of which are incorporated by reference herein, may be used. In still other embodiments, an anti-obesity device of the present invention may be through an endoscope, a catheter or sheath. In yet other embodiments, a delivery device is employed which includes a fiber optic or a chip which allows visualization of the placement of an anti-obesity device of the present invention. In still other embodiments, a balloon catheter may be employed to deliver an anti-obesity device to a bodily lumen and, more particularly, the alimentary canal. In still other embodiments, delivery of an anti-obesity device of the present invention may be unassisted (i.e., no wire or endoscope is employed). Moreover, the delivery device may have variable stiffness.

The following embodiments or aspects of the invention may be combined in any fashion and combination and be within the scope of the present invention, as follows:

Embodiment 1

A device for diverting passage of food through an alimentary canal comprising: a tubular structure comprising an outer surface and an inner surface, a proximal end and a distal end, and a central portion, wherein said proximal end of said structure is sized to fit within an esophagus, and wherein said distal end is sized to fit within an intestine.

Embodiment 2

The device of embodiment 1, wherein at least a portion of said structure is impermeable or semi-permeable to stomach fluids.

Embodiment 3

The device of embodiment 1, further comprising at least one retainer structure.

Embodiment 4

The device of embodiment 3, wherein said retainer structure secures said proximal end of said structure within said esophagus.

Embodiment 5

The device of embodiment 3, wherein said retainer structure secures said distal end of said structure within said small intestine.

Embodiment 6

The device of embodiment 1, further comprising at least one structure which is capable of expanding within said stomach.

Embodiment 7

The device of embodiment 6, wherein said at least one structure which is capable of expanding within said stomach is positioned about said structure comprising an outer surface and an inner surface, a proximal end and a distal end, and a central portion.

Embodiment 8

The device of embodiment 7, wherein said structure which is capable of expanding within the stomach is a mechanical expanding device.

Embodiment 9

The device of embodiment 7, wherein said structure which is capable of expanding within the stomach is an inflatable structure.

Embodiment 10

The device of embodiment 9, wherein said structure which is capable of expanding within the stomach is a balloon.

Embodiment 11

The device of embodiment 1, wherein said tubular structure comprises at least one distensible portion.

Embodiment 12

The device of embodiment 11, wherein said distensible portion is a pouch.

Embodiment 13

The device of embodiment 1, wherein said structure is a tubular structure.

Embodiment 14

The device embodiment 13, wherein said tubular structure is a stent.

Embodiment 15

The device of embodiment 1, wherein said tubular structure is a distensible structure.

Embodiment 16

The device of embodiment 1, wherein said tubular structure is a bag-like structure.

Embodiment 17

The device of embodiment 1, wherein said device further comprises at least one adjustable structure which is positioned about said tubular structure.

Embodiment 18

The device of embodiment 1, wherein at least a portion of said tubular structure comprises a coating which is impermeable or semi-permeable to gastric fluids.

Embodiment 19

The device of embodiment 1, further comprising a loose fabric structure attached to the outer surface of the tubular structure.

Embodiment 20

A method for diverting food within an alimentary canal in a patient comprising: (i) inserting a tubular structure having an outer surface and an inner surface, a proximal end and a distal end, and a central portion within a stomach; (ii) positioning said tubular structure within said stomach such that said proximal end of said tubular structure is positioned within an esophagus which leads to said stomach; (iii) passing said central portion and said distal portion through a wall of said stomach such that said central portion of said tubular structure transverses said stomach from said esophagus to a small intestine external to said stomach; and (iv) re-inserting the distal portion of said tubular structure through a wall of a small intestine such that said distal portion of said tubular structure is positioned within a small intestine which receives digestive fluids flowing from said stomach.

Embodiment 21

A device for inducing weight loss in a patient comprising: (i) at least one inner structure comprising a membrane which is impermeable or semi-permeable to gastric secretions; and (ii) at least one outer structure which is permeable to gastric secretions.

Embodiment 22

A method for inducing weight loss in an individual comprising positioning the device of embodiment 19 within the gastrointestinal system of a patient.

Embodiment 23

A device for inducing weight loss in a patient comprising: (i) at least one first panel comprising a proximal end and a distal end; (ii) at least one second panel comprising a proximal end and a distal end; and (iii) a channel therebetween;
wherein said proximal end of said first panel is aligned with said proximal end of said second panel to form a portion suitable for insertion in an esophagus; and
wherein said distal end of said first panel is aligned with said second end of said second panel to form a portion suitable for insertion in a small intestine.

Embodiment 24

The device of embodiment 23, wherein at least one of said first panel and said second panel is impermeable or semi-permeable to stomach fluids.

Embodiment 25

A method for inducing weight loss comprising the step of inserting the device of embodiment 23 into the gastrointestinal system of a patient.

Embodiment 26

A method for inducing weight loss in a patient comprising the steps of: (i) placing at least one restrictive device in the esophagus of said patient; (ii) placing a device having an outer surface and an inner surface, a proximal end and a distal end, and a central portion into the gastrointestinal system of the patient, and (iii) positioning said device within said gastrointestinal system such that said proximal end of said device is positioned within the esophagus, such that said distal end of said device is positioned within the small intestine, and such that the central portion of said device transverses the stomach externally.

While various embodiments of the present invention are specifically illustrated and/or described herein, it will be appreciated that modifications and variations of the present invention may be effected by those skilled in the art without departing from the spirit and intended scope of the invention.

What is claimed is:

1. A device for diverting passage of food through an alimentary canal comprising:
    an elongated element having a channel extending therethrough from a proximal end to a distal end, the proximal end being sized and shaped so that, when inserted to a desired position, an outer surface of the proximal end engages an inner surface of an esophagus adjacent an opening of a stomach, the distal end being sized and shaped so that, when inserted to the desired position, an outer surface of the distal end engages an inner surface of a duodenum, the elongated element being constructed to have rate of permeability with respect to digestion fluids no greater than a predetermined maximum permeability to reduce a level of absorption of food, the elongated element including a distensible area positionable within the stomach, the distensible area having a diameter increased with respect to portions of the elongated element proximal and distal thereto so that food passing through the elongated element will be stored in the distensible area for a period of time; and
    a first retainer sized and shaped to retain the elongated element at the desired position relative to the esophagus and duodenum.

2. The device of claim 1, wherein the maximum rate of permeability is selected to allow a predetermined partial absorption of digestion fluids.

3. The device of claim 1, wherein the first retainer is an expandable element sized and shaped for insertion within the elongated element.

4. The device of claim 3, wherein the first retainer is formed as one of a sponge and an inflatable balloon.

5. The device of claim 1, wherein the first retainer is positioned about an outer surface of the elongated element.

6. The device claim 5, wherein the first retainer is one of a stent and an anchoring balloon.

7. The device of claim 1, wherein an outer surface of the elongated element is one of partially and completely coated.

8. The device of claim 1, further comprising a loose fabric structure attached to an outer surface of the elongated element.

9. The device of claim 1, wherein the first retainer is sized and shaped to be positioned adjacent the proximal end of the elongated element.

10. The device of claim 9, further comprising a second retainer sized and shaped to the positioned adjacent the distal end of the elongated element.

11. The device of claim 1, wherein the first retainer is formed as one of a circumferential groove and a protuberance on an outer surface of the elongated element.

12. The device of claim 1, wherein a first portion of the first retainer is one of roughened and knurled to aid in anchoring thereof within the body.

13. The device of claim 1, wherein the first retainer is one of (a) an elongated arcuate anchor transversely secured to the elongated body, the anchor being configured to extend radially outward from the elongated element, (b) a suture and (c) an adhesive.

14. The device of claim 1, further comprising an adjustable band positioned over an outer wall of the elongated element to adjust a diameter thereof.

15. The device of claim 6, wherein the stent is formed of elongate filaments that are one of braided, wound and arranged in a zig-zag pattern.

16. The device of claim 6, wherein the stent comprises one or both of an outer covering and an inner liner.

17. The device of claim 1, wherein the distensible area is formed as a pouch.

18. A device for diverting passage of food, comprising:
    an elongated element having a channel extending therethrough from a proximal end to a distal end, the proximal end being sized and shaped so that, when inserted to a desired position, an outer surface of the proximal end engages an inner surface of an esophagus adjacent an opening of a stomach, the distal end being sized and shaped so that, when inserted to the desired position, an outer surface of the distal end engages an inner surface of a duodenum, the elongated element being constructed to have rate of permeability with respect to digestion fluids no greater than a predetermined maximum permeability to reduce a level of absorption of food, a portion of the channel being enlarged as a distensible area such that a diameter of the portion of the channel of the distensible area is increased with respect to portions of the channel proximal and distal thereto, the distensible area structured so that food passing through the elongated element will be stored therein for a period of time; and
    a retainer sized and shaped to retain the elongated element at the desired position relative to the esophagus and duodenum.

* * * * *